US010865172B1

(12) United States Patent
Boone

(10) Patent No.: US 10,865,172 B1
(45) Date of Patent: Dec. 15, 2020

(54) AROMATIC ENOL ETHERS

(71) Applicant: Eastman Chemical Company, Kingsport, TN (US)

(72) Inventor: Matthew Allen Boone, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/559,871

(22) Filed: Sep. 4, 2019

(51) Int. Cl.
| | |
|---|---|
| C07C 43/00 | (2006.01) |
| C09D 7/00 | (2018.01) |
| C08K 5/00 | (2006.01) |
| C07C 43/166 | (2006.01) |
| C09D 7/63 | (2018.01) |
| C09D 7/65 | (2018.01) |
| C08L 9/04 | (2006.01) |
| C08K 5/06 | (2006.01) |
| C08L 9/08 | (2006.01) |

(52) U.S. Cl.
CPC ............. *C07C 43/166* (2013.01); *C09D 7/63* (2018.01); *C09D 7/65* (2018.01); C08K 5/06 (2013.01); C08L 9/04 (2013.01); C08L 9/08 (2013.01)

(58) Field of Classification Search
CPC ............ C07C 43/166; C09D 7/65; C08K 5/06
See application file for complete search history.

(56) References Cited

U.S. PATENT DOCUMENTS

| | | | |
|---|---|---|---|
| 2,578,724 | A | 12/1951 | Mertzweiller |
| 4,839,413 | A | 6/1989 | Kiehlbauch et al. |
| 4,927,876 | A | 5/1990 | Coogan et al. |
| 4,939,233 | A | 7/1990 | Jenkins et al. |
| 4,946,932 | A | 8/1990 | Jenkins |
| 5,053,556 | A | 10/1991 | Ohnishi |
| 5,137,961 | A | 8/1992 | Goos et al. |
| 5,247,040 | A | 9/1993 | Amick et al. |
| 5,296,530 | A | 3/1994 | Bors et al. |
| 5,484,849 | A | 1/1996 | Bors et al. |
| 6,451,380 | B1 | 9/2002 | Speece, Jr. et al. |
| 6,743,748 | B2 | 6/2004 | Mizuno et al. |
| 7,208,545 | B1 | 4/2007 | Brunner et al. |
| 9,932,486 | B1 | 4/2018 | Cogar et al. |
| 2009/0035696 | A1 | 2/2009 | Matsuoka |
| 2009/0076311 | A1 | 3/2009 | Sato et al. |
| 2012/0289721 | A1 | 11/2012 | End et al. |
| 2015/0239816 | A1 | 8/2015 | Zaragoza Doerwald et al. |

FOREIGN PATENT DOCUMENTS

| | | |
|---|---|---|
| EP | 0 492 847 A2 | 7/1992 |
| WO | WO 2007/094922 A2 | 8/2007 |

OTHER PUBLICATIONS

Co-pending U.S. Appl. No. 16/559,842, filed Sep. 4, 2019; Boone.
Co-pending U.S. Appl. No. 16/559,887, filed Sep. 4, 2019; Boone.
Co-pending U.S. Appl. No. 16/559,912, filed Sep. 4, 2019; Boone.
Co-pending U.S. Appl. No. 16/559,897, filed Sep. 4, 2019; Boone.
Co-pending U.S. Appl. No. 16/559,880, filed Sep. 4, 2019; Boone et al.
Co-pending U.S. Appl. No. 16/559,859, filed Sep. 4, 2019; Boone et al.
Co-pending U.S. Appl. No. 16/560,146, filed Sep. 4, 2019; Boone et al.
Co-pending U.S. Appl. No. 16/560,161, filed Sep. 4, 2019; Boone et al.
Co-pending U.S. Appl. No. 16/559,977, filed Sep. 4, 2019; Boone.
Co-pending U.S. Appl. No. 16/559,988, filed Sep. 4, 2019; Boone et al.
ASTM D1544; Standard Test Method for Color of Transparent Liquids (Gardner Color Scale).
ASTM D2354-10$^{e1}$; Standard Test Method for Minimum Film Formation Temperature (MFFT) of Emulsion Vehicles.
ASTM D4946; Standard Test Method for Blocking Resistance of Architectural Paints.
ASTM D6886; Standard Test Method for Determination of the Weight Percent Individual Volatile Organic Compounds in Waterborne Air-Dry Coatings by Gas Chromatography.
Burczyk, B. et al.; "Relations between chemical structure and surface activity I: Synthesis and properties of aqueous solutions of acetals formed from aliphatic aldehydes and monoalkyl ethers of ethylene glycols;" Tenside Detergents; 15(2); 1978; pp. 68-71.
Burczyk, B. et al.; "Surface Properties of Selected Linear and Cyclic Acetals;" Tensioactivos: Biodegradabilidad, Fis.-Quim. Apl., Jorn. Com. Esp. Deterg.; 11$^{th}$; 1980; pp. 581-601.
Cohen, R. et al.; "Foam stabilizing properties of linear acetals containing oxyethylene units in their molecules;" Tenside Detergents; 18 (4); 1981; pp. 202-205.
Duchene, A. et al.; "Alxoxyméthyltributylétains précurseurs d'alcoxyméthyllithiums : application à la synthèse de monoéthers d'α-glycols et à l'homologation de cétones en aldéhydes;" Bulletin De La Societe Chimique De France; 1985; No. 5; pp. 787-792.
Getzkin, AJ. et al.; "Synthesis of Some Symmetrical Aldehyde Glycol Monoether Acetals;" Journal of the American Pharmaceutical Association, Scientific Edition; 49; 1960; pp. 746-750.
Kanno, T. et al.; "Oxygenation of Aromatic Vinyl Ethers. A Noticeable Formation of Epoxides and Reaction Mechanism;" Bull. Chem. Soc. Jpn.; 54; 1981; pp. 2330-2336.
Moszner, N. et al.; "Reaction behavior of monomeric β-ketoesters. 2. Synthesis, characterization and polymerization of methacrylate group containing enamines;" Polymer Bulletin; 32; pp. 419-426; (1994).

(Continued)

*Primary Examiner* — Sikarl A Witherspoon
(74) *Attorney, Agent, or Firm* — Matthew W. Smith

(57) ABSTRACT

Disclosed are aromatic enol ethers that have utility as film-hardening additives for coating formulations. The aromatic enol ethers have particular utility as film-hardening additives for water-based coating formulations. The aromatic enol ethers provide improvements in hardness and hardness related properties such as block resistance without contributing to the volatile organic content of the composition.

16 Claims, No Drawings

(56) References Cited

OTHER PUBLICATIONS

Presidential Green Chemistry Challenge: 2005 Designing Greener Chemical Award; Archer Daniels Midland Company; Archer RC™: A Nonvolatile, Reactive Coalescent for the Reduction of VOCs in Latex Paints; United States Environmental Protection Agency; Accessed via the web on Jun. 6, 2018; https://www.epa.gov/greenchemistry/presidential-green-chemistry-challenge-2005-designing-greener-chemicals-award.
Robinson, M. et al.; "Epoxide ring-opening and Meinwald rearrangement reactions of epoxides catalyzed by mesoporous aluminosilicates;" Organic & Biomolecular Chemistry; 2009; 7; pp. 2559-2564.
Safa, K. et al.; "1,4-bis[2,2-bis(trimethylsilyl)ethenyl]benzene: Regioselective ring opening of its a,B-eposybix(silane) with some nucleophiles;" Journal of Organometallic Chemistry; 694; 20019; pp. 1907-1911.
Smith, O.W. et al.; "New vinyl ester monomers for emulsion polymers;" Progress in Organic Coatings; 22; 1993; pp. 19-25.
Sokolowski, A. et al.; "Acetals and Ethers. Part IV*. Synthesis of Acetals from Aliphatic Aldehydes and Monoalkyl Ether of Ethylene Glycols;" Polish Journal of Chemistry (formerly Roczniki Chemii); 53(4); 1979; pp. 905-912.
Sokolowski, A. et al.; "Statistical Evaluation of the Influence of Linear Acetal Structures on Their Adsorption at the Aqueous Solution-Air Interface;" Comunicaciones presentadas a las XII Jornadas del Comite Espanol de la Detergencia; Asociacion De Investigacion De Detergentes, Tens; 1981; pp. 491-507.
USPTO Notice of Allowance dated Nov. 1, 2019 received in co-pending U.S. Appl. No. 16/559,977.
USPTO Notice of Allowance dated Dec. 10, 2019 received in co-pending U.S. Appl. No. 16/559,977.
USPTO Notice of Allowance dated Nov. 1, 2019 received in co-pending U.S. Appl. No. 16/559,988.
USPTO Notice of Allowance dated Dec. 11, 2019 received in co-pending U.S. Appl. No. 16/559,988.
USPTO Office Action dated Apr. 6, 2020 received in co-pending U.S. Appl. No. 16/559,842.
Kluge et al.; "Phosphonate Reagents for the Synthesis of Enol Ethers and One-Carbon Homologation to Aldehydes;" J. Org. Chem.; vol. 44; No. 26; 1979; pp. 4847-4852.
USPTO Office Action dated Apr. 30, 2020 received in co-pending U.S. Appl. No. 16/560,161.
Trost et al.; "Model for Asymmetric Induction in the Diels-Alder Reaction;" Journal of the American Chemical Society; vol. 102; 1980; pp. 7595-7596.
USPTO Office Action dated Jun. 1, 2020 received in co-pending U.S. Appl. No. 16/559,897.
USPTO Office Action dated Jun. 10, 2020 received in co-pending U.S. Appl. No. 16/559,912.
USPTO Notice of Allowance dated Jun. 24, 2020 received in co-pending U.S. Appl. No. 16/559,887.
USPTO Notice of Allowance dated Aug. 10, 2020 received in co-pending U.S. Appl. No. 16/559,842.
USPTO Notice of Allowance dated Aug. 17, 2020 received in co-pending U.S. Appl. No. 16/560,161.

AROMATIC ENOL ETHERS

FIELD OF THE INVENTION

This application relates to chemistry generally. In particular, this application relates to enol ethers and more particularly to aromatic enol ethers.

BACKGROUND OF THE INVENTION

Enol ethers are useful in a variety of chemical applications such as plasticizers, diluents, wetting agents and paint additives and as intermediates in chemical processes. Plasticizers, diluents, wetting agents and paint additives often are volatile and evaporate into the atmosphere during use. For example, coalescing aids that are added to water-based paints, act as temporary plasticizers in latex emulsions. The coalescing aids lower the glass transition temperature (Tg) of the latex polymer and as the paint dries, the polymers that have been softened by the coalescing aid are allowed to flow together and form a film after the water has left the system. Coalescing aids that are volatile evaporate out of the film. This allows the polymer to return to the original Tg thereby giving harder films for better block and print resistant coatings.

Due to environmental concerns, the use of volatile materials such as paint additives, plasticizers, diluents, wetting agents and coalescing aids are increasing undesirable. There is a need for materials that can be used as plasticizers, diluents, wetting agents and paint additives that exhibit low volatility.

SUMMARY OF THE INVENTION

The invention is set forth in the appended claims.

The present application relates to an enol ether compound according to Formula I:

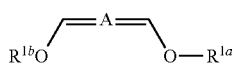

I wherein:
A is $(C_{8-20})$ alkylaryl;
$R^{1a}$ and $R^{1b}$ are independently

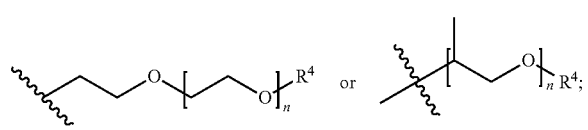

each $R^4$ is independently $(C_{1-12})$alkyl, or —C(O)$R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

The present application also relates to an enol ether compound according to Formula II:

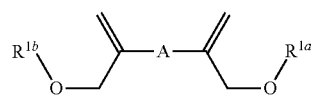

II wherein:
A is $(C_{8-20})$ aryl;
$R^{1a}$ and $R^{1b}$ are independently

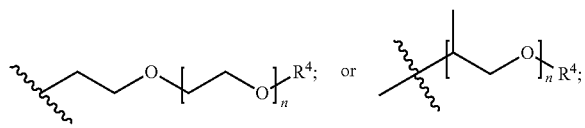

each $R^4$ is independently $(C_{1-12})$alkyl, or —C(O)$R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

The present application also relates to an enol ether compound according to Formula III:

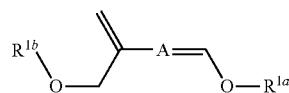

III wherein:
A is $(C_{8-20})$ alkylaryl;
$R^{1a}$ and $R^{1b}$ are independently

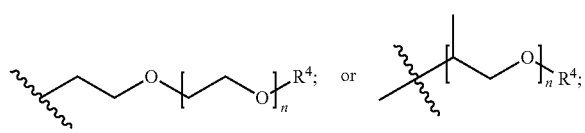

each $R^4$ is independently $(C_{1-12})$alkyl, or —C(O)$R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

DETAILED DESCRIPTION

Definitions

In this specification and in the claims that follow, reference will be made to a number of terms, which shall be defined to have the following meanings.

"Alkyl" means an aliphatic hydrocarbon. The alkyl can specify the number of carbon atoms, for example (C1-5) alkyl. Unless otherwise specified, the alkyl group can be unbranched or branched. In some embodiments, the alkyl group is branched. In some embodiments, the alkyl group is unbranched. Non-limiting examples of alkanes include methane, ethane, propane, isopropyl (i.e., branched propyl), butyl, and the like.

"Alkenyl" means an aliphatic hydrocarbon with one or more unsaturated carbon-carbon bonds. The alkenyl can specify the number of carbon atoms, for example (C2-12) alkenyl. Unless otherwise specified, the alkyl group can be unbranched or branched. In some embodiments, the alkyl group is branched. In some embodiments, the alkyl group is unbranched. Non-limiting examples of alkanes include ethenyl, propenyl, butenyl, hexa-3,5-dienyl, and the like.

"Alcohol" means a chemical containing one or more hydroxyl groups.

"Aldehyde" means a chemical containing one or more —C(O)H groups.

"Cycloalkyl" means a cyclic hydrocarbon compound. The cycloalkyl can specify the number of carbon atoms in ring system, for example (C3-8)cycloalkyl. Non-limiting examples of cycloalkyl include cyclopropyl, cyclobutyl, cyclohexyl, and cyclooctyl.

"Aryl" means a ring system made up carbon atoms that has at least one ring that is aromatic. The carbon units making up the aryl ring may be specified, for example 5- to 9-membered aryl. Non-limiting examples of aryl include phenyl, naphthyl, 2,3-dihydro-1H-indene, and 1,2,3,4-tetrahydronaphthalene.

Values may be expressed as "about" or "approximately" a given number. Similarly, ranges may be expressed herein as from "about" one particular value and/or to "about" or another particular value. When such a range is expressed, another aspect includes from the one particular value and/or to the other particular value. Similarly, when values are expressed as approximations, by use of the antecedent "about," it will be understood that the particular value forms another aspect.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

"Chosen from" as used herein can be used with "or" or "and." For example, Y is chosen from A, B, and C means Y can be individually A, B, or C. Alternatively, Y is chosen from A, B, or C means Y can be individually A, B, or C, or a combination of A and B, A and C, B and C, or A, B, and C.

Presented herein are novel enol ethers which can be used in applications such as (but not limited to) plasticizers, diluents, wetting agents, coalescing aids and paint additives.

In some embodiments the invention is a compound according to Formula I:

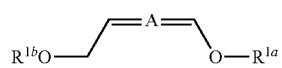

I wherein: A is $(C_{8-20})$alkylaryl;
$R^{1a}$ and $R^{1b}$ are independently

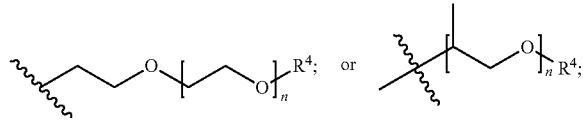

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments the invention is a compound according to Formula II.

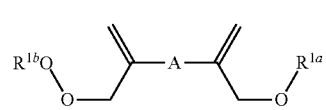

II wherein A is $(C_{8-20})$alkylaryl;
$R^{1a}$ and $R^{1b}$ are independently

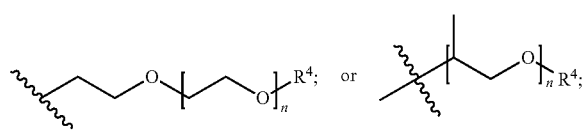

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments the invention is a compound according to Formula III:

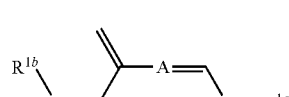

III wherein: A is (C8-20)alkylaryl;
R1a and R1b are independently

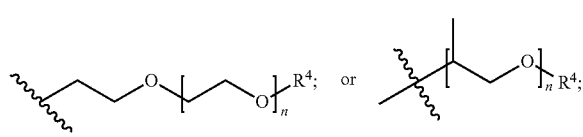

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments, A in Formulas I, II and III, is 1,2-, 1,3-, or 1,4-disubstituted phenyl. In some embodiments, each n is an integer from 1 to 3.

In some embodiments of Formulas I, II and II, each $R^4$ is hydrogen. In some embodiments, each $R^4$ is $(C_{1-12})$alkyl. In some embodiments, each $R^4$ is independently ethyl. In some embodiments, each $R^4$ is (C2-12)alkenyl. In some embodiments, each $R^4$ is —C(O)$R^5$.

In some embodiments of Formulas I, II and III, each $R^5$ is $(C_{1-12})$ alkyl unsubstituted or substituted by $R^6$. In some embodiments, each $R^5$ is $(C_{1-12})$alkenyl unsubstituted or substituted by $R^6$. In some embodiments, each $R^5$ is $(C_{3-8})$ cycloalkyl. In some embodiments, each $R^5$ is 5- to 9-membered aryl.

In some embodiments of Formulas, I, II and III, each n is an integer from 1 to 2. In some embodiments, each n is an integer from 1 to 3. In some embodiments, each n is an integer from 1 to 4. In some embodiments, each n is an integer from 1 to 5. In some embodiments, n is an integer from 1 to 6. In some embodiments, n is an integer from 1 to 7. In some embodiments, n is an integer from 1 to 8. In some embodiments, n is an integer from 1 to 9. In some embodiments, n is an integer from 1 to 10. In some embodiments, n is an integer from 1 to 11. In some embodiments, n is an integer from 1 to 12. In some embodiments, n is an integer from 1 to 13. In some embodiments, n is an integer from 1 to 14. In some embodiments, n is an integer from 1 to 15.

In some embodiments, the compounds of Formulas I, II and III have a volatile organic content of less than 50 wt % according to ASTM D6886. In some embodiments, the volatile organic content is less than 30 wt %. In some embodiments, the volatile organic content is less than 10 wt %. In some embodiments, the volatile organic content is less than 5 wt %. In some embodiments, the volatile organic content is less than 3 wt %. In some embodiments, the volatile organic content is less than 2 wt %. In some embodiments, the volatile organic content is less than 1 wt %. In some embodiments, the volatile organic content is less than 0.8 wt %.

Compositions

The enol ether compounds disclosed in the present application exhibit a low volatile organic content (less than 50 wt %, but as low as 0.7 wt % according to ASTM D6886). The enol ethers can be used as reactive film-hardening compounds. Reactive film-hardening compounds react with components in coating compositions to form crosslinks in the films providing improved film properties. When we say that the enol ether compounds of this invention can be used as reactive film-hardening additives, we mean when added to a coating composition, that a harder film is obtained upon curing the composition than is obtained in the absence of the invention enol ether additives, or that the coating composition exhibits a higher gel fraction than in the absence of the enol ether additive, or that both coating composition hardness and increased gel fraction properties are improved by the addition of the enol ether reactive film-hardening additives.

Not wishing to be bound by any theory, the increase in hardness observed in a coating that contains the enol ether additives described herein may be the result of a chemical reaction, so that the additives described herein may be described as "reactive" enol ether film-hardening additives.

The enol ether materials described herein can also facilitate the individual latex particles coming together to form a continuous film at a given temperature by reducing the minimum film-forming temperature (MFFT) of the latex polymer.

In some embodiments, the composition comprises the compounds represented by Formulas I, II and II.

In some embodiments, the compounds of Formula I, II and III are enol ethers represented by Formulas 5-21:

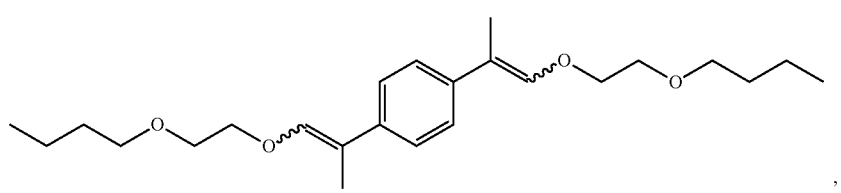

5

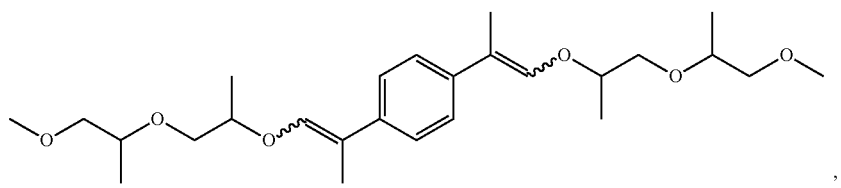

6

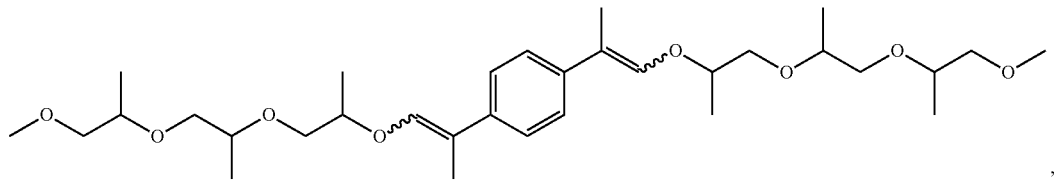

7

-continued
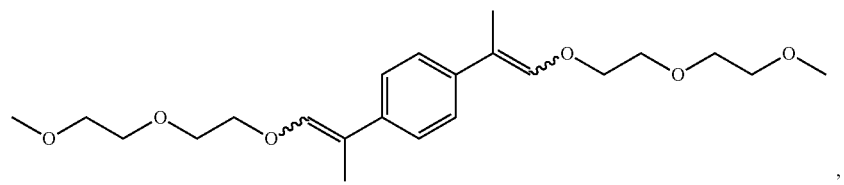
8
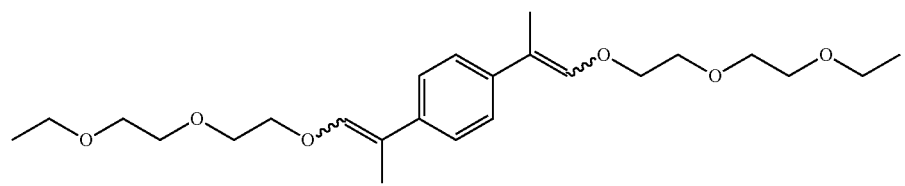
9
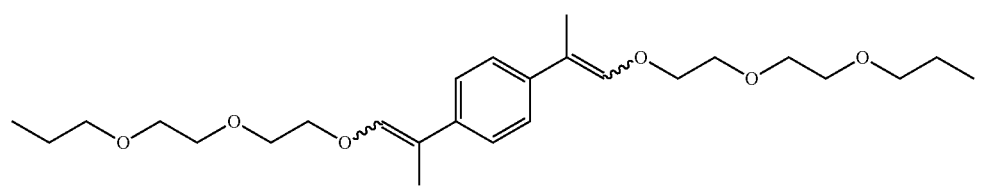
10
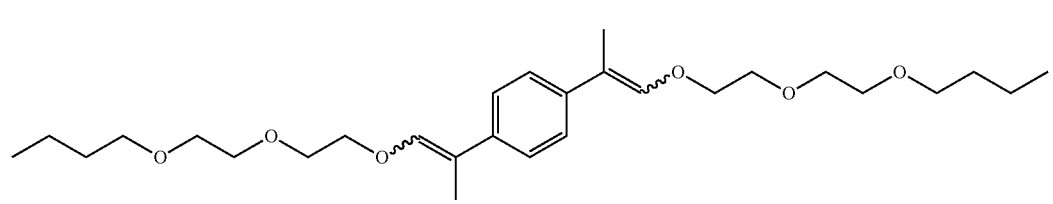
11
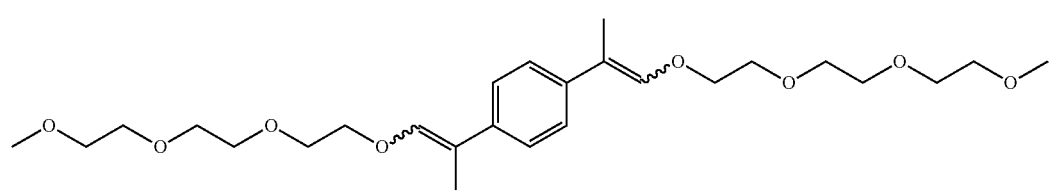
12
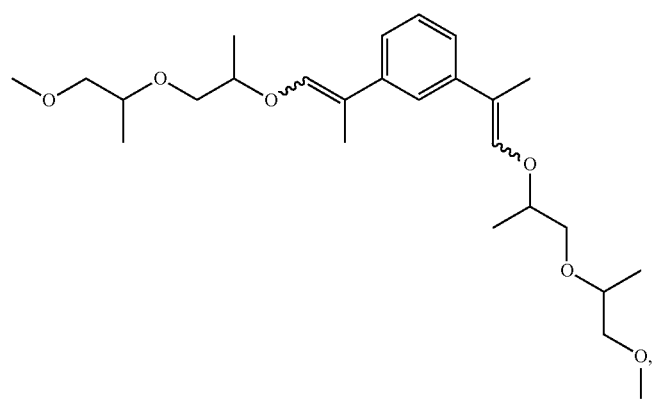
13

-continued
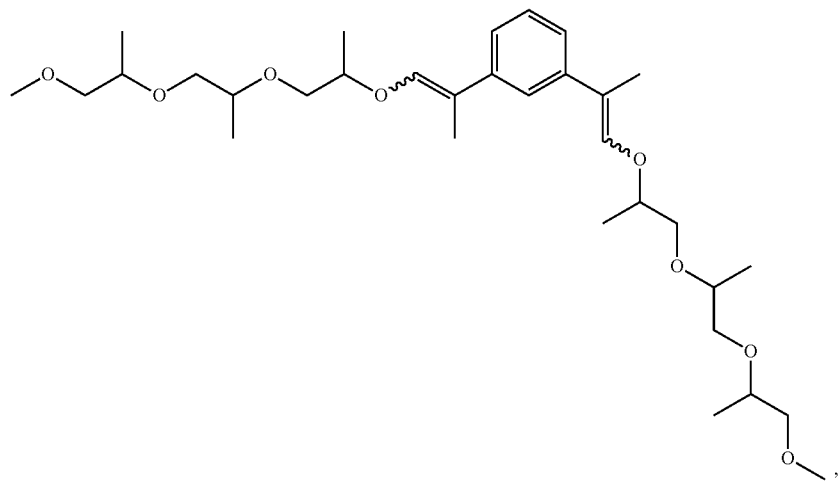
14
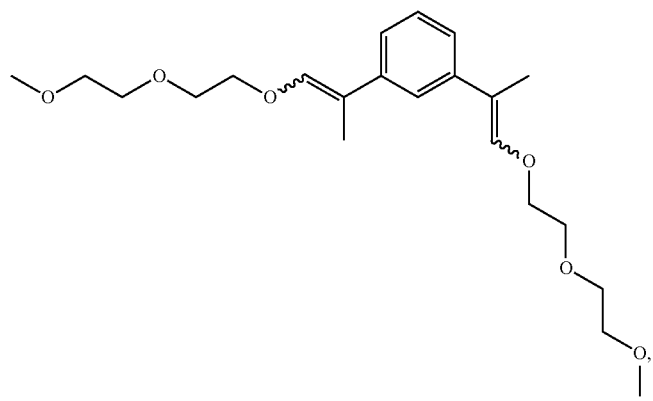
15
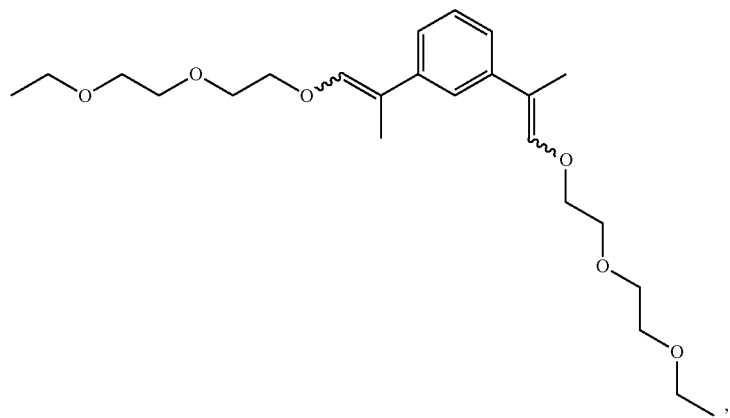
16

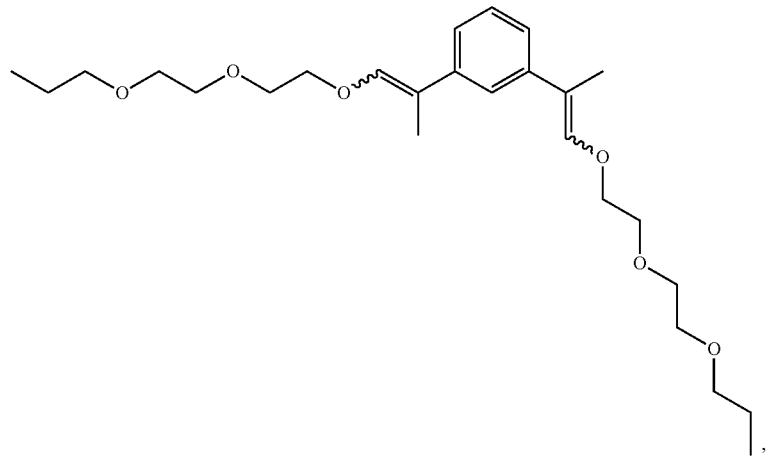
17
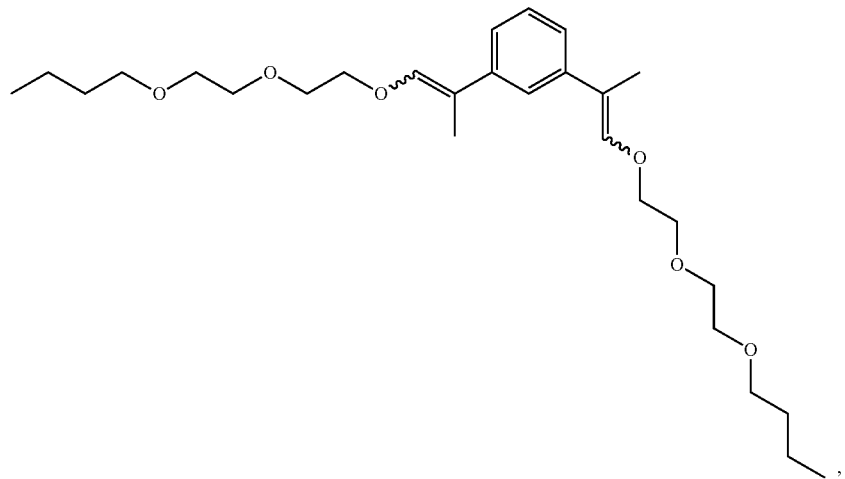
18
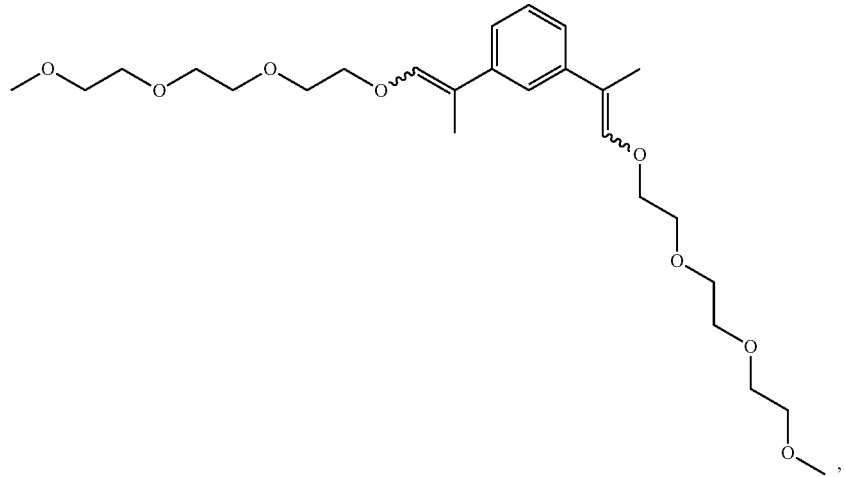
19

The enol ethers depicted by Formulas 5-19 are representative of the enol ethers claimed herein. Isomers of the enol ethers depicted by Formulas 5-19 are expected to be produced during synthesis of the enol ethers depicted by Formulas 5-19. All isomers of the enol ethers depicted by Formulas 5-19 and are within the scope of the claims set forth herein.

The compounds depicted by Formulas I, II and III include those having a weight percent volatile content of less than 50%, as measured according to ASTM Method D6886. This test may be conducted generally by heating the sample in a forced air oven at 110° C. for 60 minutes. The weight loss after the test is deemed to result from a loss of volatiles originally present in the sample; the percent volatile present in the original sample may then be calculated. Although the cited test can be conducted on coating compositions containing other components such as latex polymers, the values cited herein may be obtained from a sample of the additive itself. The weight percent volatile of a film-hardening aid may be used herein as a yardstick to measure the amount of VOC the additive would contribute to the VOC in a particular end use such as a component of a coating composition.

EXAMPLES

This invention can be further illustrated by the following examples thereof, although it will be understood that these examples are included merely for purposes of illustration and are not intended to limit the scope of the invention unless otherwise specifically indicated. In particular more than one method to make enol ethers is available to the skilled artisan. Methods A and B are described herein.

Abbreviations:

mL is milliliter; wt % is weight percent; eq is equivalent(s); hrs or h is hour(s); mm is millimeter; m is meter; GC is gas chromatography; ° C. is degree Celsius; min is minute; $t_R$ is retention time; VOC is volatile organic compound; MeP is methyl palmitate; w/v is weight/volume; μL is microliter. RFHA is reactive film-hardening additive.

Method A: Dialdehyde Method

Preparation of dicarbinol [1] and 2,2'-(1,4-phenylene)dipropanal [2]

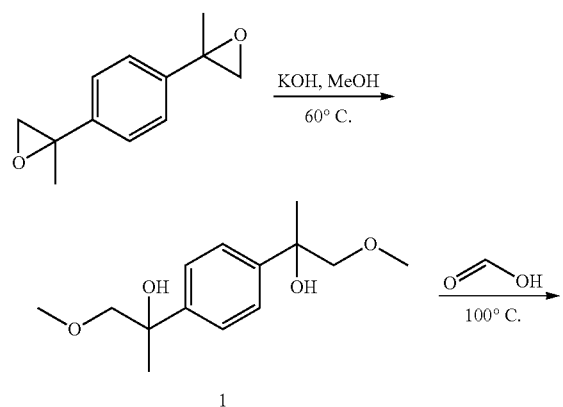

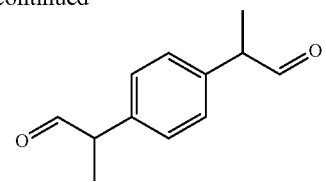

Preparation of Dicarbinol 1

KOH (49.2 g, 788 mmol) was dissolved in MeOH (400 mL) contained within a 1 L, 4-necked round-bottom flask fitted with thermocouple, overhead stirrer, and nitrogen inlet atop a reflux condenser. During the addition of KOH, internal temperature reached 60° C. and was maintained there by heating mantle. The solid di-epoxide was added over the course of 1.5 hrs. The reaction was monitored by $^1$H NMR (aliquot was taken and dissolved in DMSO-$d_6$). Once di-epoxide was completely consumed, the reaction was cooled to ambient temperature, and acetic acid (47.3 g, 788 mmol) was added dropwise. Once addition was complete, the volatiles were removed under reduced pressure using a rotary evaporator. The residue was taken up in 250 mL of toluene and then washed with 250 mL of water. The aqueous layer was back-extracted with 250 mL of EtOAc (ethyl acetate). The organics were combined, dried with MgSO$_4$ and simultaneously treated with 5 g of activated carbon. The mixture was filtered and volatiles were removed under reduced pressure using a rotary evaporator. Dicarbinol 1 was isolated as a white solid. LC-MS (Column A) $t_R$: 3.80 min (Exact mass: 254.15 m/z, found 254.2 m/z).

Preparation of 2,2'-(1,4-phenylene)dipropanal [2]

The dicarbinol 1 was then dissolved in formic acid (88%, 98.0 g) contained within a 500 mL, 4-necked round-bottom flask fitted with thermocouple, overhead stirrer, and nitrogen inlet atop a reflux condenser. The mixture was heated to 100° C. After 6 hrs, additional formic acid was added (98.0 g). After an additional 2 hrs, GC indicated >99% conversion to dialdehyde 2. The volatiles were then removed under reduced pressure using a rotary evaporator. The residue was taken up in 250 mL of toluene and then washed with a saturated solution of NaHCO$_3$. After layer separation, the organics were dried with MgSO$_4$, filtered, and then concentrated. The crude material was then Kugelrohr—distilled at 150° C./1 mm Hg to isolate the di-aldehyde 2 as a colorless oil. GC-MS $t_R$: 14.47 min (Exact mass: 190.10 m/z, found: 190.1 m/z).

Preparation of 2,2'-(1,3-phenylene)dipropanal 4

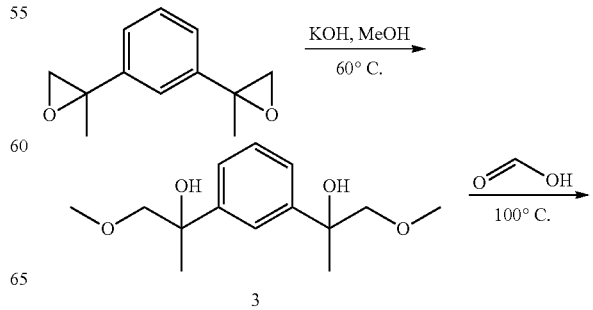

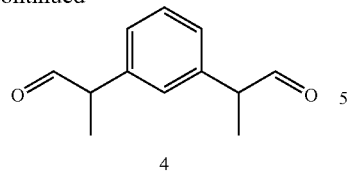

4

Dicarbinol 3 was prepared in a similar manner to dicarbinol 2 using procedure described in Method A. [LC-MS (Column B) $t_R$: 4.55 min, 4.68 min (Exact mass: 254.15 m/z, found 254.2 m/z)]. Di-aldehyde 4 was prepared in a similar manner to di-aldehyde 2 using Method A.

GC-MS $t_R$: 14.22 min (Exact mass: 190.10 m/z, found: 190.1 m/z).

Method of Enol Ether Preparation:

Di-aldehyde was added to a nitrogen-swept, round-bottom flask fitted with overhead-stirrer, thermocouple, and Dean-Stark. Glycol alcohol solvent (5 equiv.) was added all at once, followed by the addition of toluene (2× mass of aldehyde used). Sodium methanesulfonate (0.025 equiv.) was added to the flask, followed by the addition of methanesulfonic acid (0.025 equiv.). The reaction was heated to reflux and held at that temperature for 15 hrs. Toluene was removed under reduced pressure using a rotary evaporator. Then 50% caustic (0.024 equiv.) was added all at once. The mixture was fractionally distilled under reduced pressure.

Example 1: Preparation of (E,E/Z,Z)-1,4-bis(1-(2-butoxyethoxy)prop-1-en-2-yl)benzene [5]

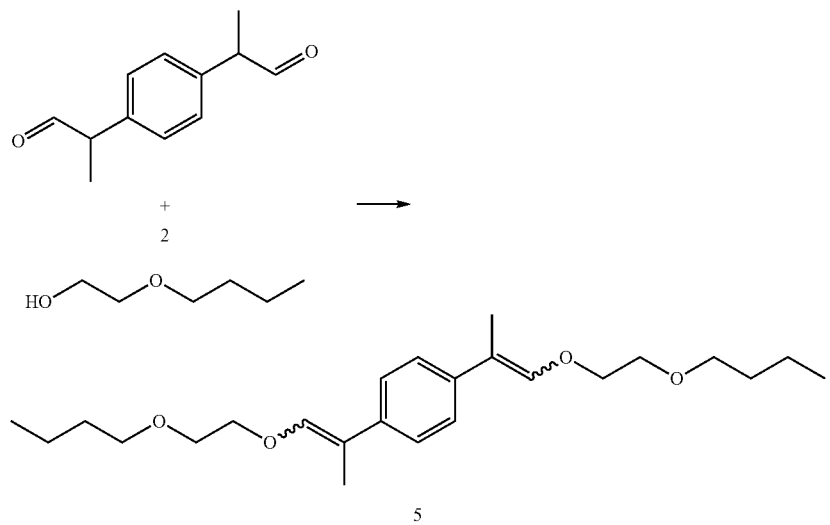

GC-MS $t_R$: 22.83 min, 24.34 min, 26.08 min (Exact mass: 390.28 m/z, found 390.3 m/z).

Example 2: Preparation of (E,E/Z,Z)-1,4-bis(1-((1-((1-methoxypropan-2-yl)oxy)propan-2-yl)oxy)prop-1-en-2-yl)benzene [6]

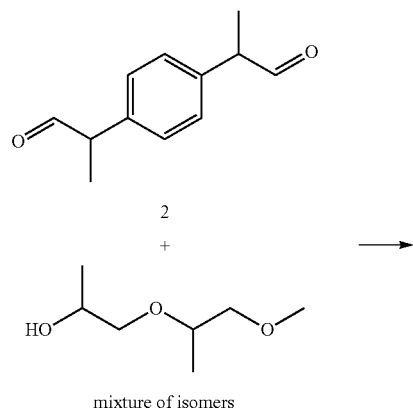

mixture of isomers

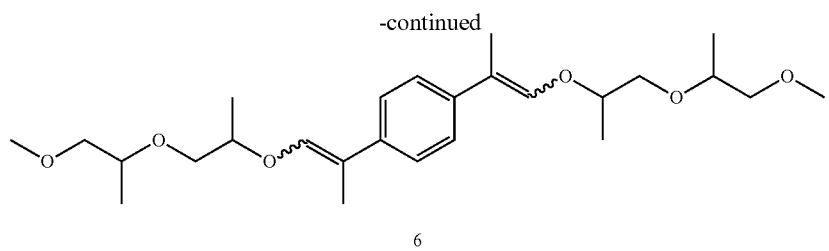

6

GC-MS $t_R$: 25.8 min, 26.2 min, 28.3 min, 28.9 min (Exact mass: 450.30 m/z, found 450 m/z).

Method B:

To a 4-necked round-bottom flask fitted with an overhead stirrer, thermocouple, and nitrogen inlet was added acetic anhydride (5 equiv.) and sodium bisulfate monohydrate (0.025 equiv.). The mixture was then heated to 65° C. and held for 30 minutes. The dicarbinol was then added dropwise over the course of 4-5 hrs via a pressure-equalizing addition funnel. Once the addition was complete, the reaction was checked by GC. Once complete, the mix was transferred to a 1-neck round-bottom flask and the excess acetic anhydride/acetic acid was removed under reduced pressure using a rotary evaporatory. The crude was taken up in toluene. The organics were then washed with 10% caustic (×2) solution and then 5% ammonium hydroxide solution. The mixture was dried with $MgSO_4$ and simultaneously treated with activated carbon. After filtration, the volatiles were removed under reduced pressure using a rotary evaporator. Light-boiling impurities were removed by distillation. The enol ether/1,1-disubstituted olefin was Kugelrohr-distilled to afford product blends.

Example 3: A Mixture of (E,E/Z,Z)-1,4-bis(1-((1-((1-methoxypropan-2-yl)oxy)propan-2-yl)oxy)prop-1-en-2-yl)benzene [6a], (E,Z)-1-(1-((1-((1-methoxypropan-2-yl)oxy)propan-2-yl)oxy)prop-1-en-2-yl)-4-(3-((1-((1-methoxypropan-2-yl)oxy)propan-2-yl)oxy)prop-1-en-2-yl)benzene [6b], and 1,4-bis(3-((1-((1-methoxypropan-2-yl)oxy)propan-2-yl)oxy)prop-1-en-2-yl)benzene [6c]

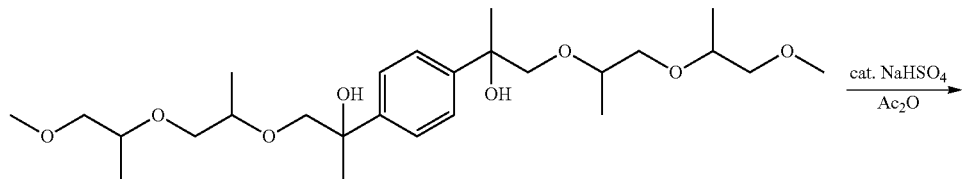

6

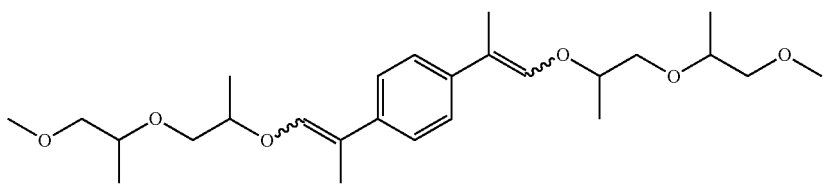

6a

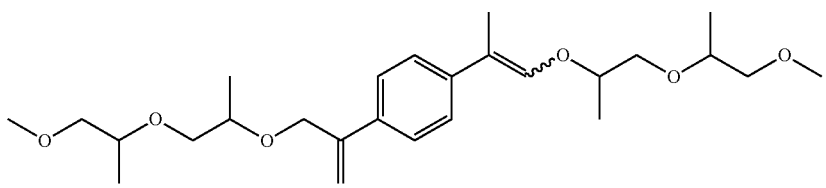

6b

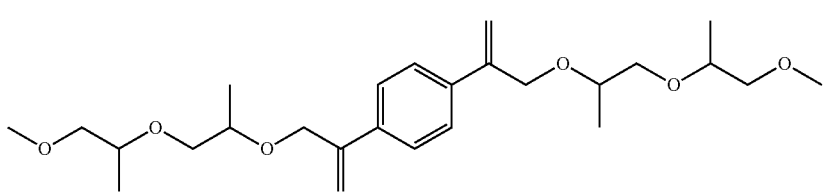

6c

GC-MS $t_R$: 25.80 min, 26.28 min, 26.80 min, 27.30 min, 28.38 min, 28.94 min (Exact mass: 450.30 m/z, found: 450.4 m/z).
Example 4: A Mixture of (E,E/Z,Z)-1,4-bis(4,7,10-trimethyl-2,5,8,11-tetraoxatetradec-12-en-13-yl)benzene [7a], (E,Z)-4,7,10-trimethyl-13-(4-(4,7,10-trimethyl-2,5,8,11-tetraoxatetradec-13-en-13-yl)phenyl)-2,5,8,11-tetraoxatetradec-12-ene [7b], and 1,4-bis(4,7,10-trimethyl-2,5,8,11-tetraoxatetradec-13-en-13-yl)benzene [7c]
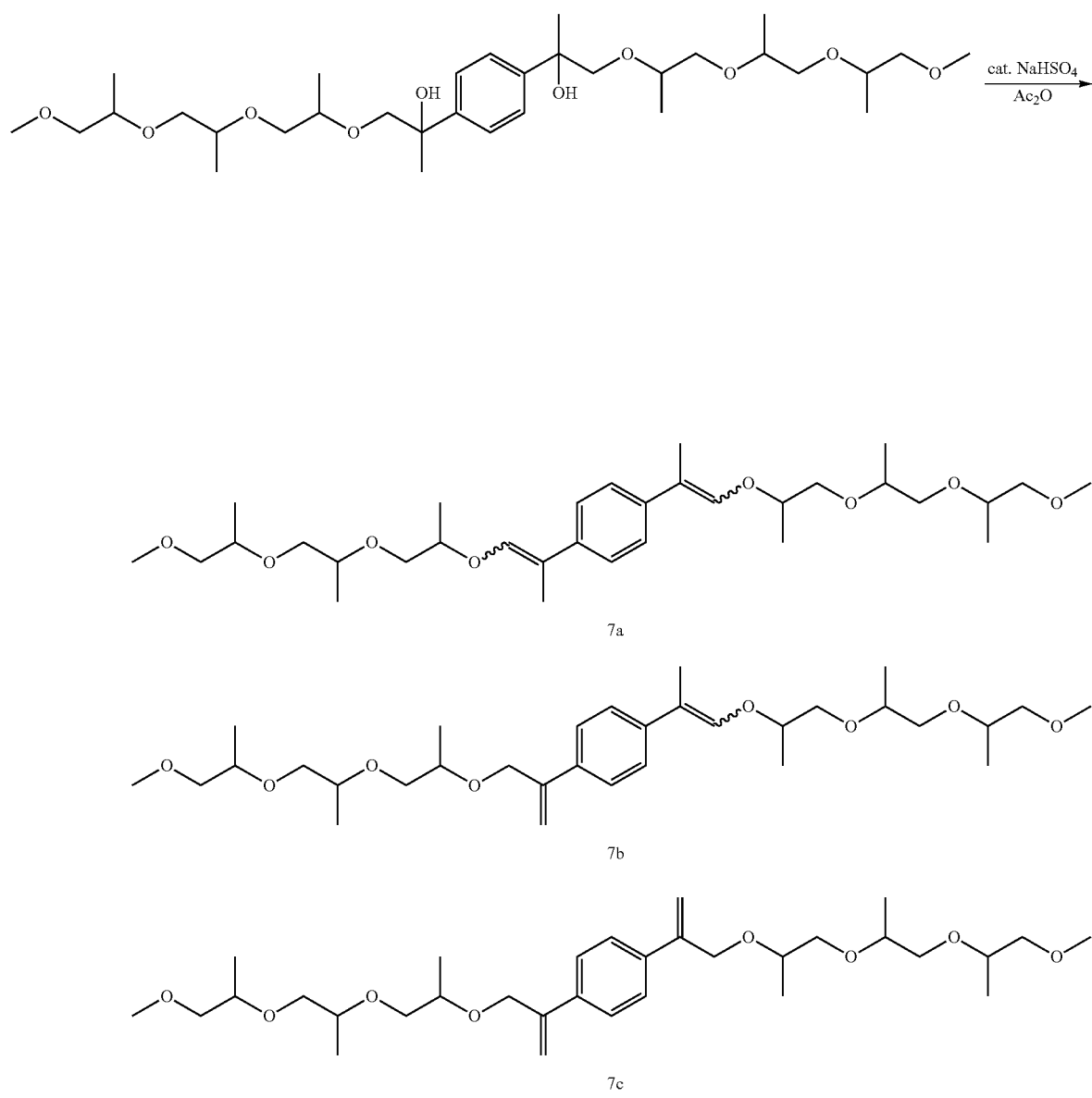

GC-MS $t_R$: 43.08 (broad peak), 69.53 min (broad peak) (Exact mass: 566.38 m/z, found: 566.5 m/z).
Example 5: A Mixture of (E,E/Z,Z)-1,4-bis(1-(2-(2-methoxyethoxy)ethoxy)prop-1-en-2-yl)benzene [8a], (E,Z)-1-(1-(2-(2-methoxyethoxy)ethoxy)prop-1-en-2-yl)-4-(3-(2-(2-methoxyethoxy)ethoxy)prop-1-en-2-yl)benzene [8b], and 1,4-bis(3-(2-(2-methoxyethoxy)ethoxy)prop-1-en-2-yl)benzene [8c]
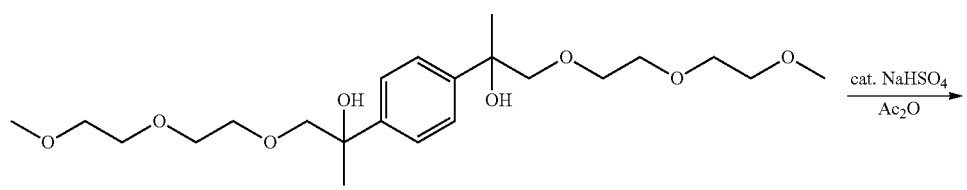
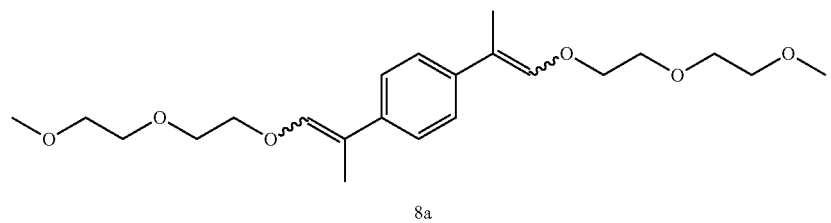
8a
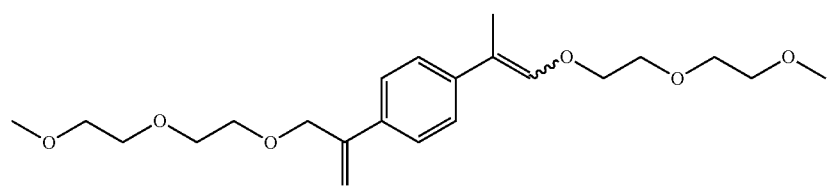
8b
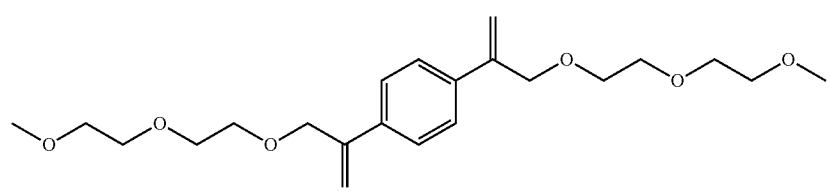
8c GC-MS $t_R$: 23.9 min, 24.29 min, 24.48 min, 25.64 min, 25.96 min, 27.63 min (Exact mass: 394.24 m/z, found: 394.3 m/z).
Example 6: A Mixture of (E,E/Z,Z)-1,4-bis(1-(2-(2-ethoxyethoxy)ethoxy)prop-1-en-2-yl)benzene [9a], (E/Z)-1-(1-(2-(2-ethoxyethoxy)ethoxy)prop-1-en-2-yl)-4-(3-(2-(2-ethoxyethoxy)ethoxy)prop-1-en-2-yl)benzene [9b], and 1,4-bis(3-(2-(2-ethoxyethoxy)ethoxy)prop-1-en-2-yl)benzene [9c]
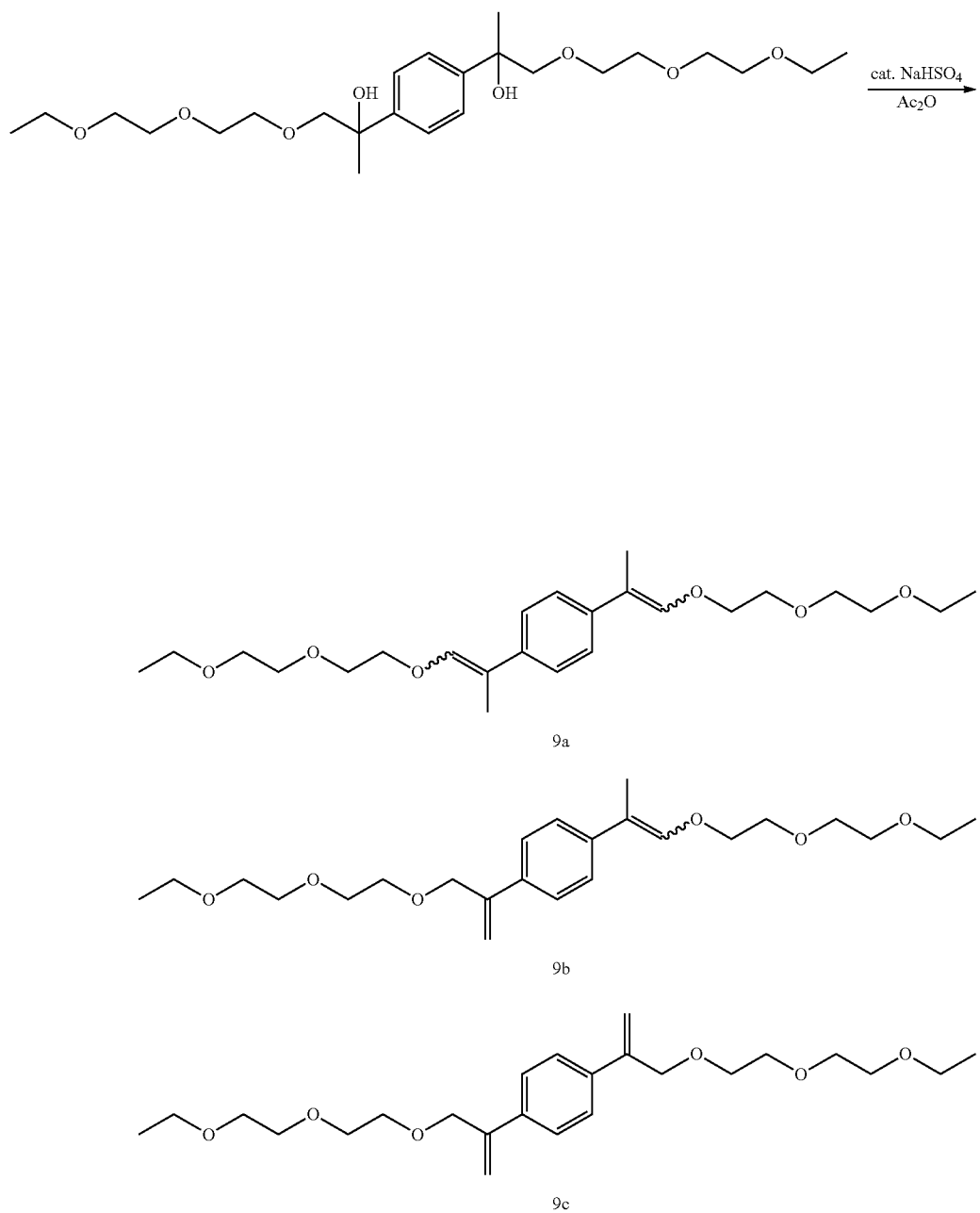

GC-MS $t_R$: 25.64 min, 26.23 min, 26.55 min, 28.00 min, 28.47 min, 30.67 min (Exact mass: 422.27 m/z, found: 422.3 m/z).
Example 7: A Mixture of (E,E/Z,Z)-1,4-bis(1-(2-(2-propoxyethoxy)ethoxy)prop-1-en-2-yl)benzene [10a], (E,Z)-1-(1-(2-(2-propoxyethoxy)ethoxy)prop-1-en-2-yl)-4-(3-(2-(2-propoxyethoxy)ethoxy)prop-1-en-2-yl)benzene [10b], 1,4-bis(3-(2-(2-propoxyethoxy)ethoxy)prop-1-en-2-yl)benzene [10c]
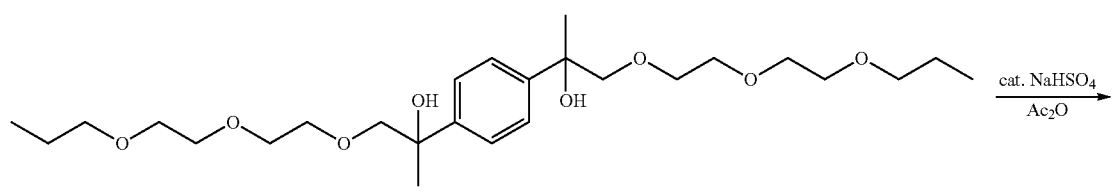
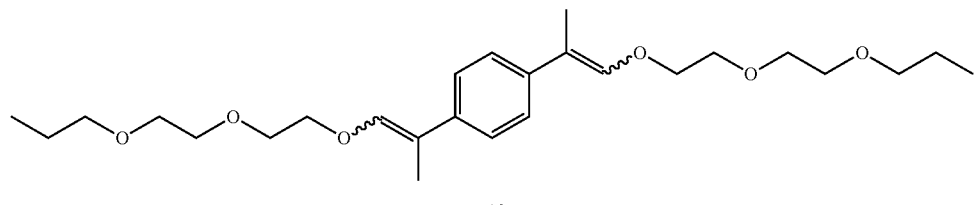
10a
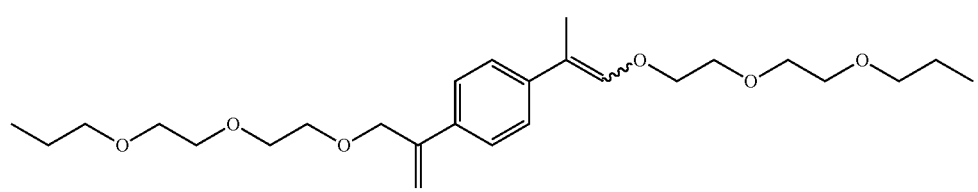
10b
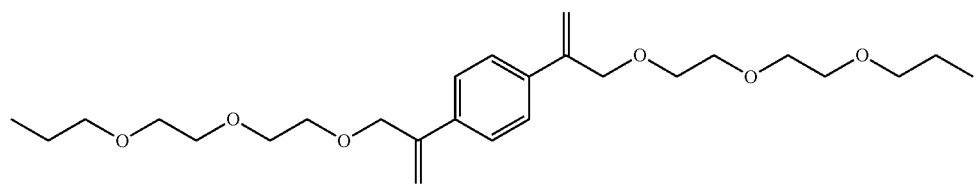
10c GC-MS $t_R$: 29.70 min, 30.67 min, 31.30 min, 33.27 min, 34.18 min, 37.58 min (Exact mass: 450.30 m/z, found: 450.3 m/z).
Example 8: A Mixture of (E,E/Z,Z)-1,4-bis(1-(2-(2-butoxyethoxy)ethoxy)prop-1-en-2-yl)benzene [11a], (E,Z)-1-(1-(2-(2-butoxyethoxy)ethoxy)prop-1-en-2-yl)-4-(3-(2-(2-butoxyethoxy)ethoxy)prop-1-en-2-yl)benzene [11b], 1,4-bis(3-(2-(2-butoxyethoxy)ethoxy)prop-1-en-2-yl)benzene [11c]
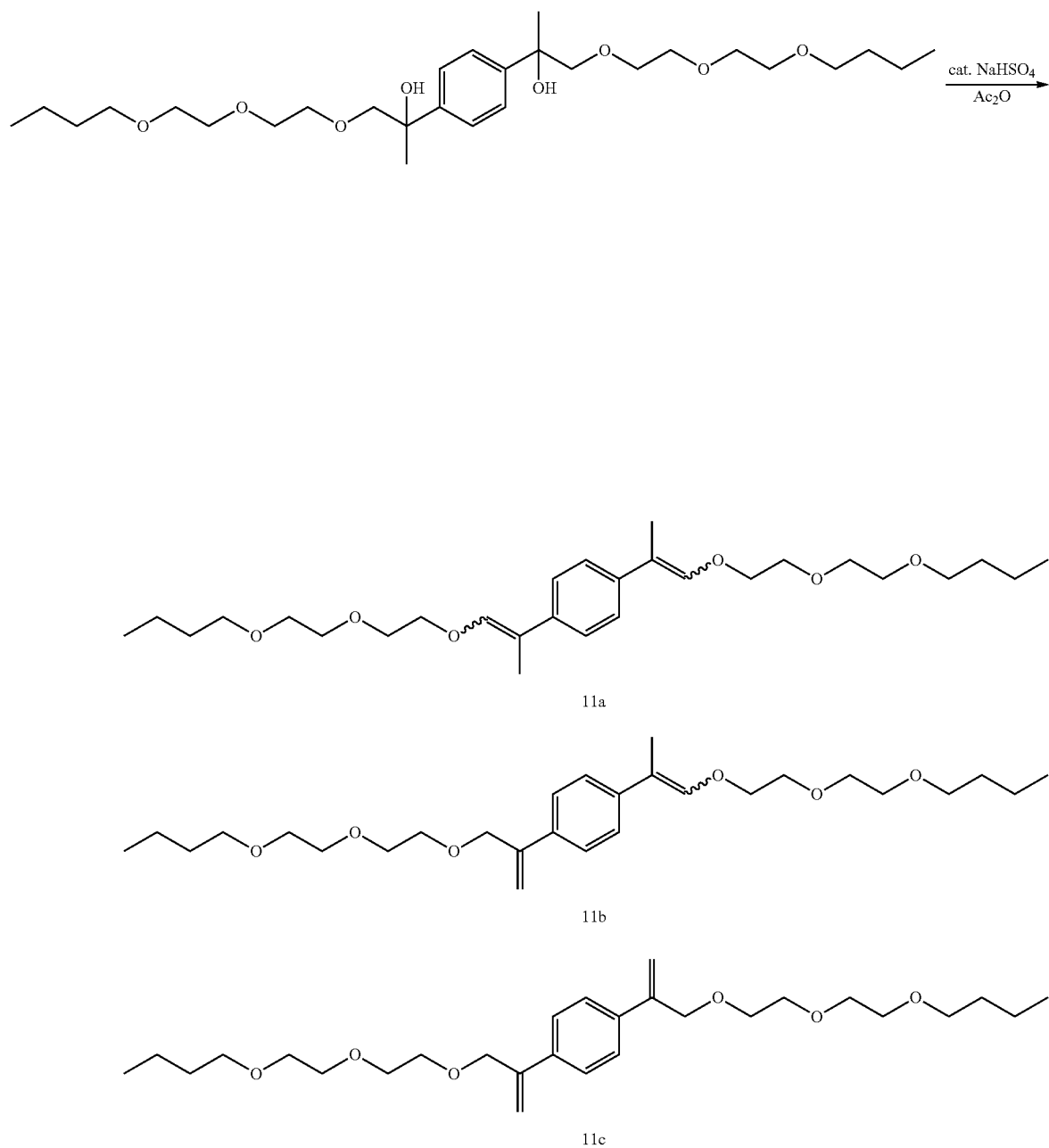

GC-MS $t_R$: 36.07 min, 37.71 min, 38.86 min, 41.45 min (Exact mass: 478.33 m/z, found: 478.4 m/z).
Example 9: A Mixture of (E,E/Z,Z)-1,4-di(2,5,8,11-tetraoxatetradec-12-en-13-yl)benzene [12a], (E,Z)-13-(4-(2,5,8,11-tetraoxatetradec-13-en-13-yl)phenyl)-2,5,8,11-tetraoxatetradec-12-ene [12b], and 1,4-di(2,5,8,11-tetraoxatetradec-13-en-13-yl)benzene [12c]
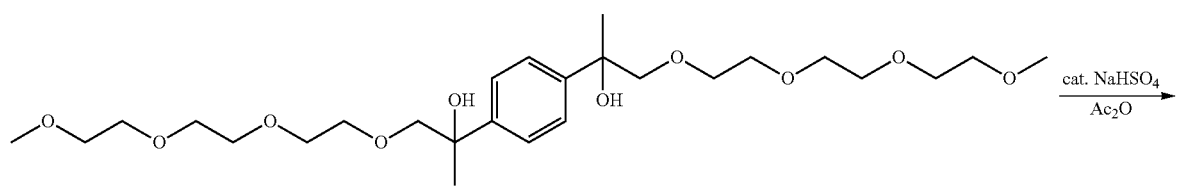
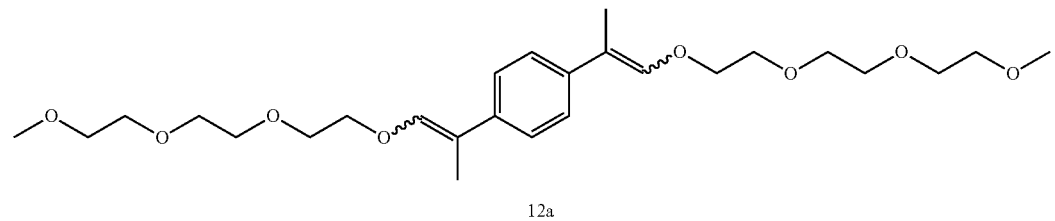
12a
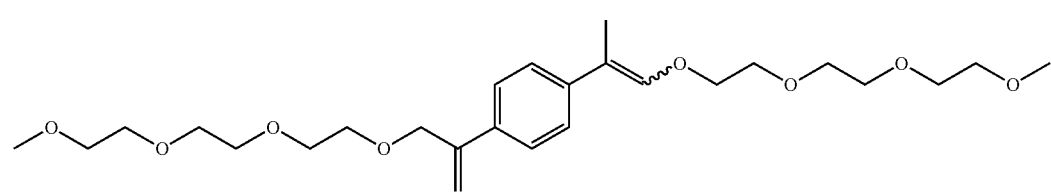
12b
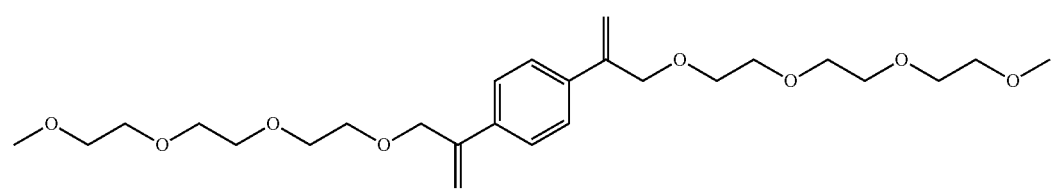
12c GC-MS $t_R$: 39.51 min, 41.51 min, 42.78 min, 46.43 min, 48.26 min, 55.04 min (Exact mass: 482.29 m/z, found: 482.4 m/z).
Example 10: A Mixture of (E,E/Z,Z)-1,3-bis(1-((1-((1-methoxypropan-2-yl)oxy)propan-2-yl)oxy)prop-1-en-2-yl)benzene [13a], (E/Z)-1-(1-((1-((1-methoxypropan-2-yl)oxy)propan-2-yl)oxy)prop-1-en-2-yl)-3-(3-((1-((1-methoxypropan-2-yl)oxy)propan-2-yl)oxy)prop-1-en-2-yl)benzene [13b], and 1,3-bis(3-((1-((1-methoxypropan-2-yl)oxy)propan-2-yl)oxy)prop-1-en-2-yl)benzene [13c]
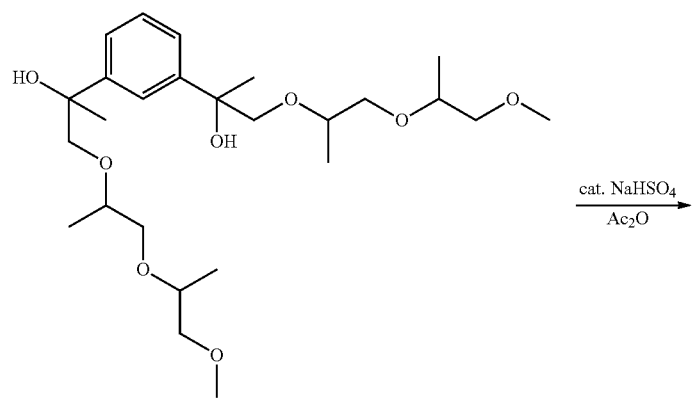
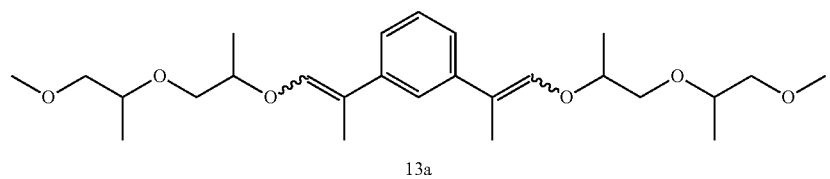
13a
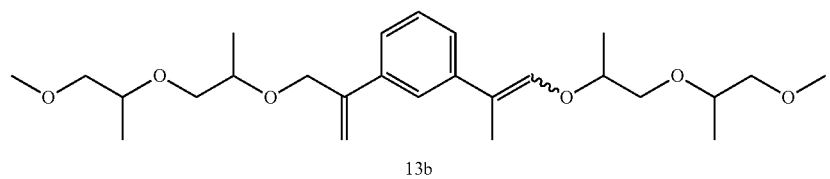
13b
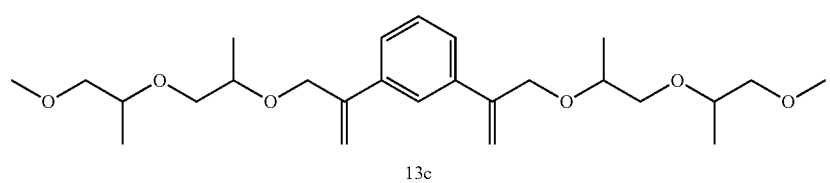
13c GC-MS $t_R$: 22.78 min, 23.14 min, 23.45 min, 23.91 min, 24.27 min, 24.59 min, 25.17 min, 25.58 min, 26.05 min (Exact mass: 450.30 m/z, found: 450.4 m/z).
Example 11: A Mixture of (E,E/Z,Z)-1,3-bis(4,7,10-trimethyl-2,5,8,11-tetraoxatetradec-12-en-13-yl)benzene [14a], (E/Z)-4,7,10-trimethyl-13-(3-(4,7,10-trimethyl-2,5,8,11-tetraoxatetradec-13-en-13-yl)phenyl)-2,5,8,11-tetraoxatetradec-12-ene [14b], and 1,3-bis(4,7,10-trimethyl-2,5,8,11-tetraoxatetradec-13-en-13-yl)benzene [14c]
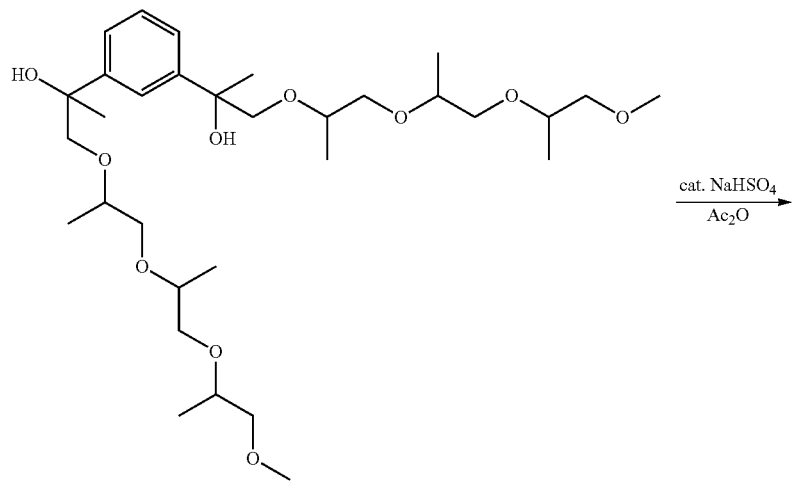
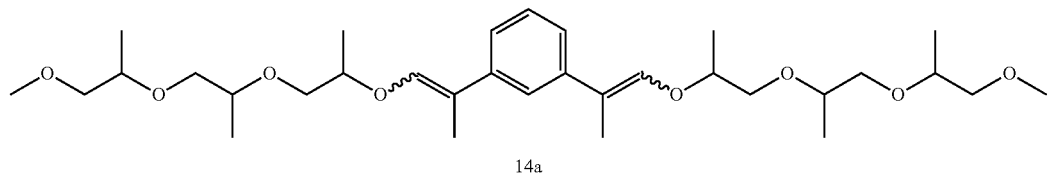
14a
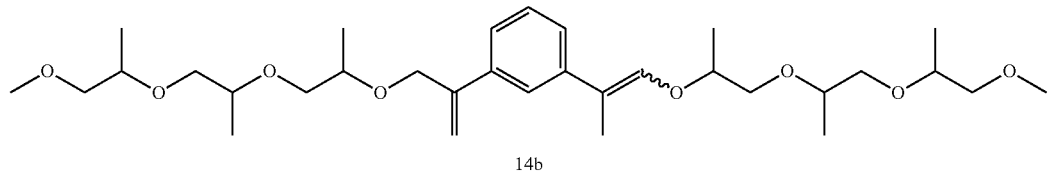
14b
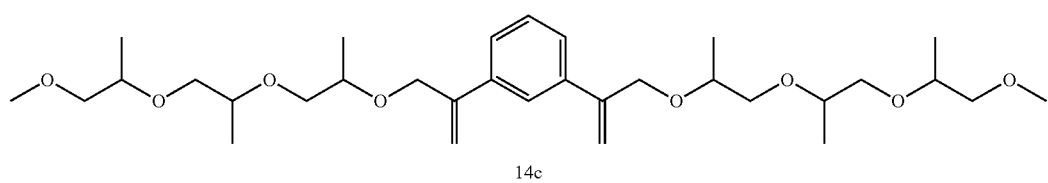
14c GC-MS $t_R$: 41.84-43.72 min (broad peak) (Exact mass: 566.38 m/z, found: 566.5 m/z).
Example 12: A Mixture of (E,E/Z,Z)-1,3-bis(1-(2-(2-methoxyethoxy)ethoxy)prop-1-en-2-yl)benzene [15a], (E/Z)-1-(1-(2-(2-methoxyethoxy)ethoxy)prop-1-en-2-yl)-3-(3-(2-(2-methoxyethoxy)ethoxy)prop-1-en-2-yl)benzene [15b], 1,3-bis(3-(2-(2-methoxyethoxy)ethoxy)prop-1-en-2-yl)benzene [15c]
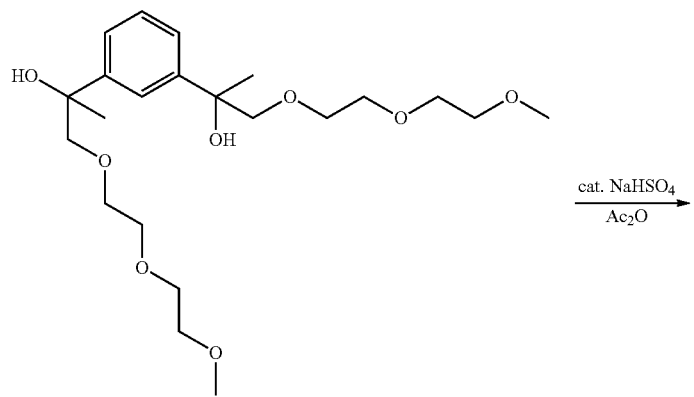
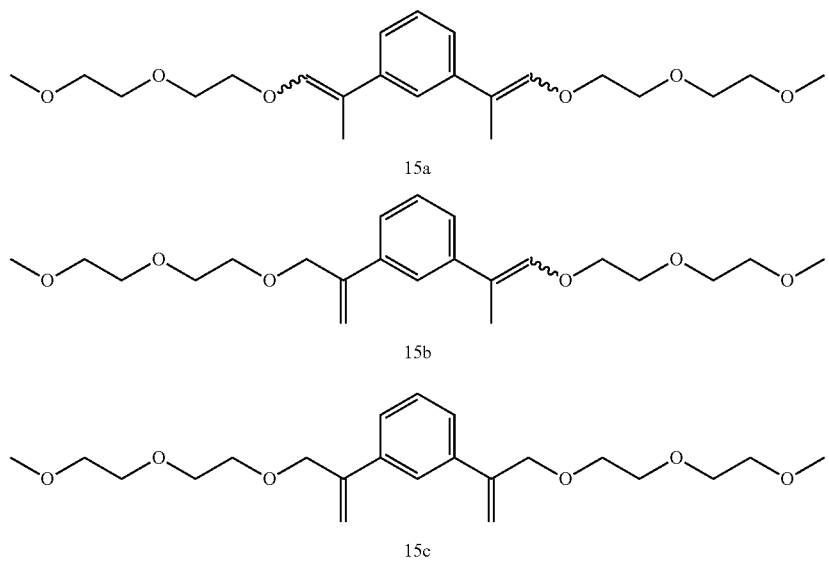
15a
15b
15c GC-MS $t_R$: 22.57 min, 22.91 min, 23.08 min, 23.79 min, 24.08 min, 25.43 min (Exact mass: 394.24 m/z, found: 394.3 m/z).
Example 13-1 and Example 13-2: A Mixture of (E,E/Z,Z)-1,3-bis(1-(2-(2-ethoxyethoxy)ethoxy)prop-1-en-2-yl)benzene [16a], (E/Z)-1-(1-(2-(2-ethoxyethoxy)ethoxy)prop-1-en-2-yl)-3-(3-(2-(2-ethoxyethoxy)ethoxy)prop-1-en-2-yl)benzene [16b], and 1,3-bis(3-(2-(2-ethoxyethoxy)ethoxy)prop-1-en-2-yl)benzene [16c]
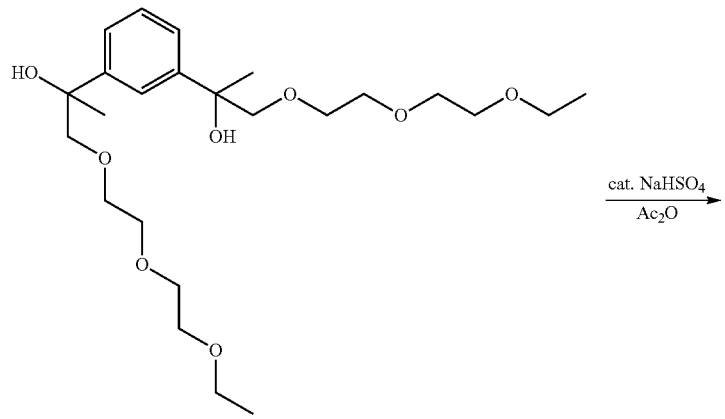
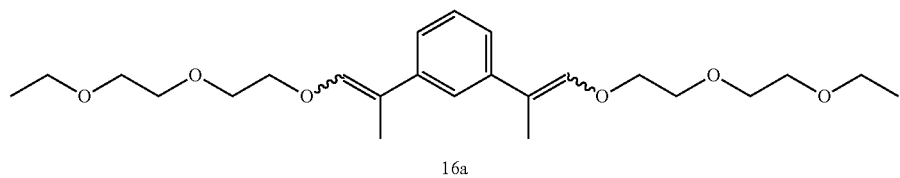
16a
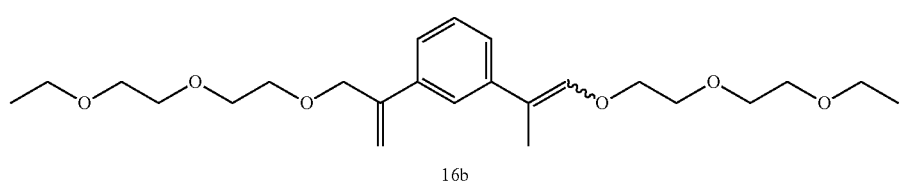
16b
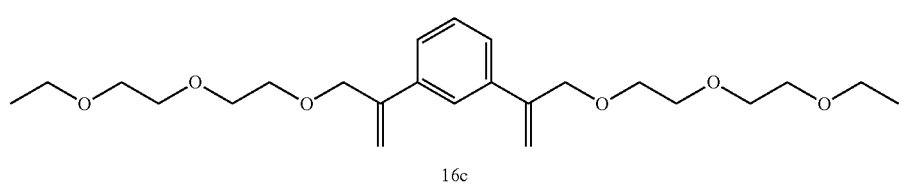
16c GC-MS $t_R$: 24.07 min, 24.73 min, 24.80 min, 25.72 min, 25.87 min, 27.78 min (Exact mass: 422.27 m/z, found: 422.3 m/z). 0.05 equiv. of sodium bisulfate used.

Example 13-1: 0.025 equiv. of sodium bisulfate used. Ratio of 16a:16b:16c=1.0:1.7:3.6.

Example 13-2: 0.50 equiv. of sodium bisulfate used. Ratio of 16a:16b:16c=1.0:2.7:10.

Example 14: A Mixture of (E,E/Z,Z)-1,3-bis(1-(2-(2-propoxyethoxy)ethoxy)prop-1-en-2-yl)benzene [17a], (E/Z)-1-(1-(2-(2-propoxyethoxy)ethoxy)prop-1-en-2-yl)-3-(3-(2-(2-propoxyethoxy)ethoxy)prop-1-en-2-yl)benzene [17b], and 1,3-bis(3-(2-(2-propoxyethoxy)ethoxy)prop-1-en-2-yl)benzene [17c]

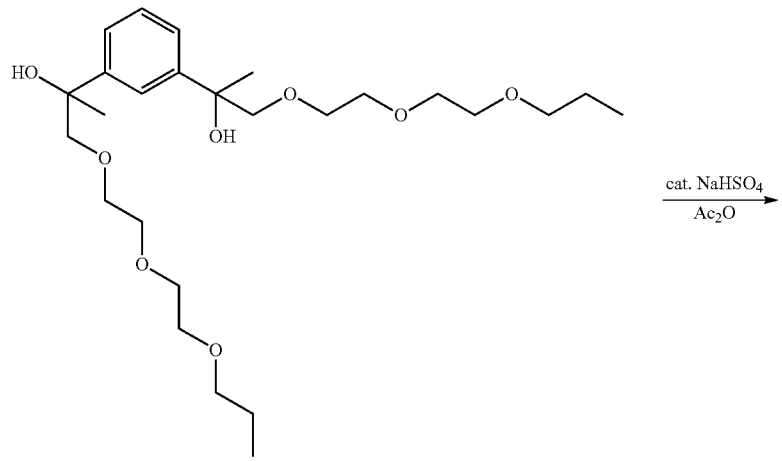

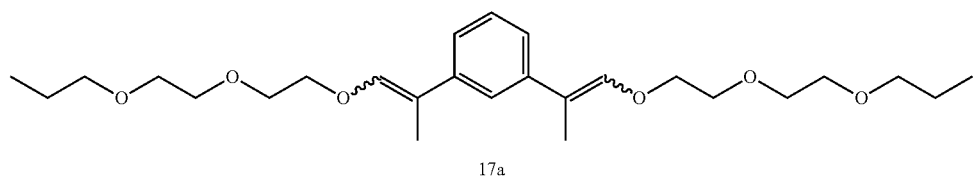

17a

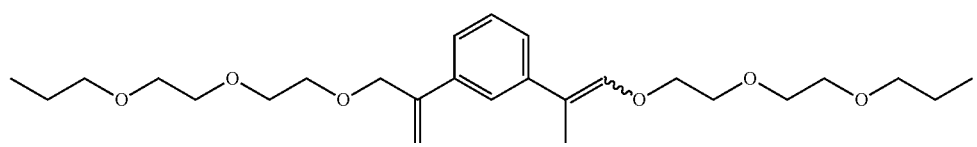

17b

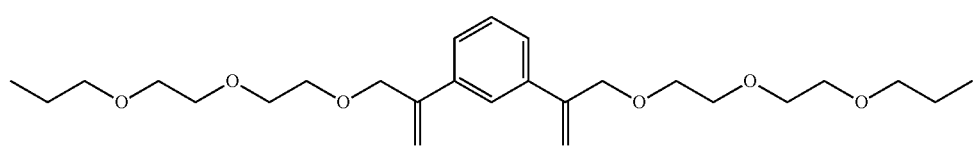

17c

GC-MS $t_R$: 27.42 min, 28.16 min, 28.63 min, 29.80 min, 30.61 min, 33.20 min (Exact mass: 450.30 m/z, found: 450.4 m/z).
Example 15: A Mixture of (E,E/Z,Z)-1,3-bis(1-(2-(2-butoxyethoxy)ethoxy)prop-1-en-2-yl)benzene [18a], (E/Z)-1-(1-(2-(2-butoxyethoxy)ethoxy)prop-1-en-2-yl)-3-(3-(2-(2-butoxyethoxy)ethoxy)prop-1-en-2-yl)benzene [18b], and 1,3-bis(3-(2-(2-butoxyethoxy)ethoxy)prop-1-en-2-yl)benzene [18c]
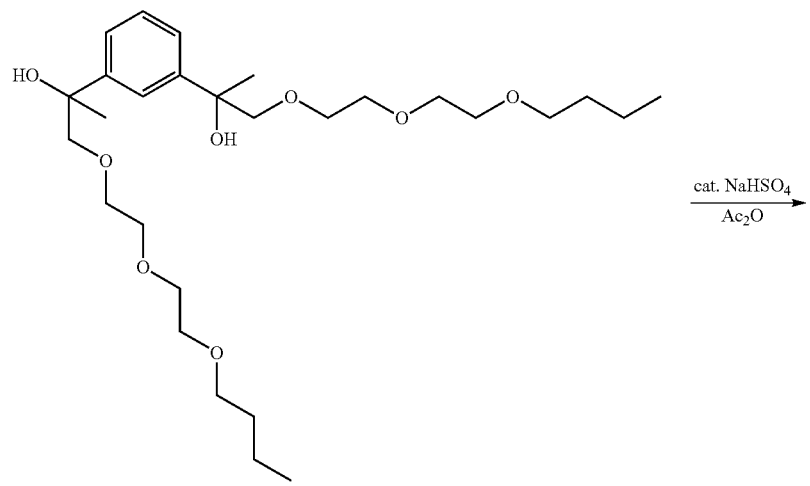
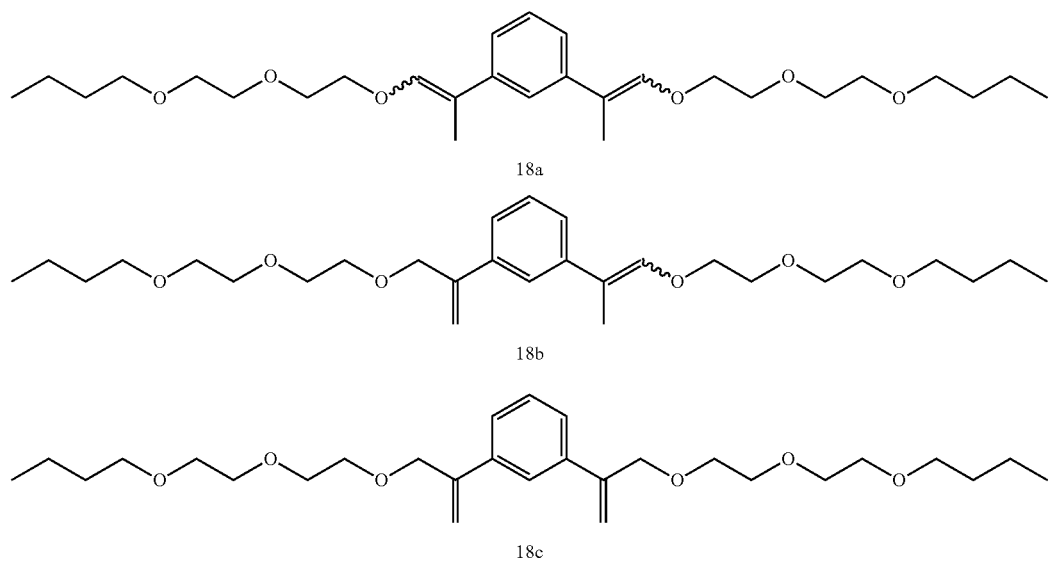

GC-MS $t_R$: 32.75 min, 33.89 min, 34.68 min, 36.20 min, 37.42 min, 41.29 min (Exact mass: 478.33 m/z, found: 478.4 m/z).

Example 16: A Mixture of (E,E/Z,Z)-1,3-di(2,5,8,11-tetraoxatetradec-12-en-13-yl)benzene [19a], (E/Z)-13-(3-(2,5,8,11-tetraoxatetradec-13-en-13-yl)phenyl)-2,5,8,11-tetraoxatetradec-12-ene [19b], and 1,3-di(2,5,8,11-tetraoxatetradec-13-en-13-yl)benzene [19c]

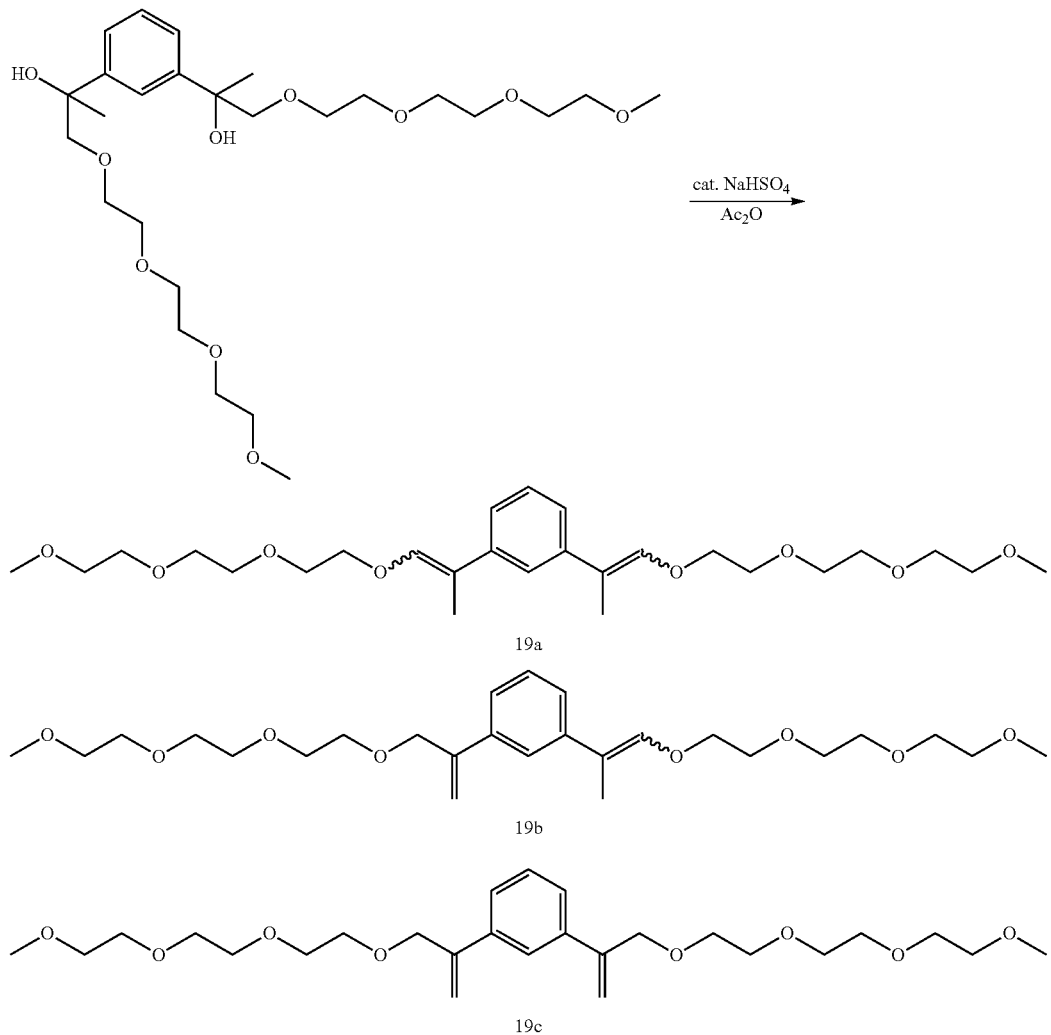

GC-MS $t_R$: 35.57 min, 36.92 min, 37.81 min, 39.66 min, 41.11 min, 45.59 min (Exact mass: 482.29 m/z, found: 482.3 m/z).

The examples described above were defined as non-VOC by ASTM D6886. This method uses MeP as a standard—if compound $t_R$>MeP $t_R$, compound is defined as non-VOC.

Conditions—Agilent 1100 LC
Sample Prep: 2-3 mg/mL in DMSO
Column A: Zorbax XDB-C18×4.6 mm, 5 μm
Column B: Poroshell EC-C18 50×4.6 mm, 2.7 μm
Column Temp: 40° C.
Injection Volume: 2 μL
DAD: 190-600 nm collection Pump Conditions: Initial—97% water (2.5 mM NH$_4$OAc) (Solvent A) and 3% acetonitrile (Solvent B)
Gradient:

| Time (min) | % Solvent A | % Solvent B | Flow (mL/min) |
|---|---|---|---|
| 0 | 97 | 3 | 1.0 |
| 10 | 0 | 100 | 1.0 |
| 25 | 0 | 100 | 1.0 |

-continued

| Time (min) | % Solvent A | % Solvent B | Flow (mL/min) |
|---|---|---|---|
| 25.1 | 97 | 3 | 1.0 |
| 30 | 97 | 3 | 1.0 |

Mass spectra were acquired with a Micromass LCT mass spectrometer, which was coupled to the LC. Mass spectra were collected using electrospray ionization in both the positive-ion and negative ion modes. Ammonium acetate (50 mM in MeOH) was added post column (0.1 mL/min) to enhance ionization efficiency. ES+/ES− scan range was 60-3300 amu (25 and 75V). GC-MS Instrument Parameters—Agilent 6890N GC with Agilent 5975B VL MSD Sample Prep: 100 A sample diluted to 1 mL with toluene; Column: DB-5 30 m×0.25 mm×0.25 μm; Oven Ramp: 0-4.5 mins at 40° C.; Ramp 20 C/min to 280 C, Hold 53.5 mins; Injector: Temperature—250° C.; Split Flow—65 mL/min; Carrier Flow Rate—1.3 mL/min; Volume—1.0 μL; MS: Transfer Line—280° C.; Ion Source Temp—230° C.; Mass Range—34-700 amu. Methyl palmitate $t_R$=16.6 min using the above method.

The invention has been described in detail with reference to the embodiments disclosed herein, but it will be understood that variations and modifications can be effected within the spirit and scope of the invention.

I claim:

1. A compound according to Formula I:

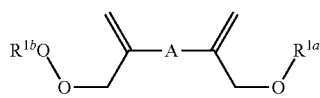

I wherein:
A is $(C_{8-20})$ alkylaryl;
$R^{1a}$ and $R^{1b}$ are independently

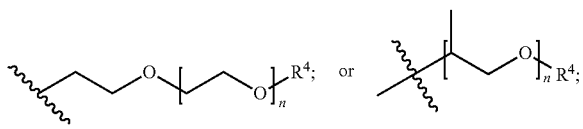

each $R^4$ is independently hydrogen, $(C_{1-12})$alkyl, or —C(O)$R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

2. The compound of claim 1 wherein A is 1,2-, 1,3-, or 1,4-disubstituted phenyl.

3. The compound of claim 1 wherein $R^4$ is hydrogen or ethyl.

4. The compound of claim 1 wherein, n is an integer from 1 to 4.

5. The compound of claim 1 wherein the composition has a volatile organic content of less than 50 wt % according to ASTM D6886.

6. A compound according to Formula II:

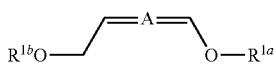

II wherein:
A is $(C_{8-20})$ aryl;
$R^{1a}$ and $R^{1b}$ are independently

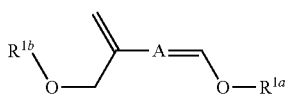

each $R^4$ is independently $(C_{1-12})$alkyl, or —C(O)$R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

7. The compound of claim 6 wherein A is 1,2-, 1,3-, or 1,4-disubstituted phenyl.

8. The compound of claim 6 wherein $R^4$ is hydrogen or ethyl.

9. The compound of claim 6 wherein, n is an integer from 1 to 4.

10. The compound of claim 6 wherein the composition has a volatile organic content of less than 50 wt % according to ASTM D6886.

11. A compound according to Formula III:

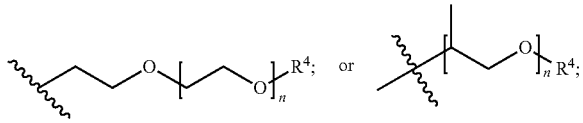

III wherein:
A is $(C_{8-20})$ alkylaryl;
$R^{1a}$ and $R^{1b}$ are independently each $R^4$ is independently (C1-12)alkyl, or —C(O)R5;
each R5 is (C1-12)alkyl unsubstituted or substituted by R6, (C2-12)alkenyl unsubstituted or substituted by R6, (C3-8)cycloalkyl, or 5- to 9-membered aryl;
each R6 is (C1-4)alkoxy, or oxo; and
each n is independently an integer from 1 to 15.

12. The compound of claim 11 wherein A is 1,2-, 1,3-, or 1,4-disubstituted phenyl.

13. The compound of claim 11 wherein $R^4$ is hydrogen or ethyl.

14. The compound of claim 11 wherein, n is an integer from 1 to 4.

15. The compound of claim 11 wherein the composition has a volatile organic content of less than 50 wt % according to ASTM D6886.

16. An enol ether compound selected from the group consisting of compositions having Formulas 5-19:
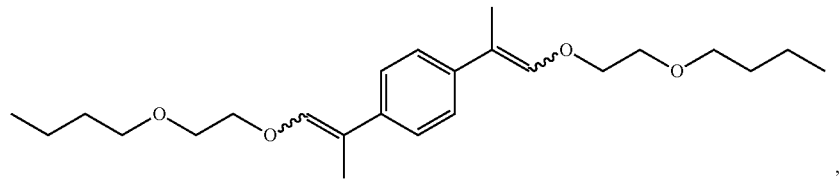
5
,
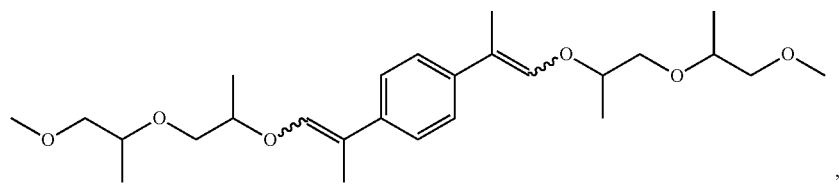
6
,
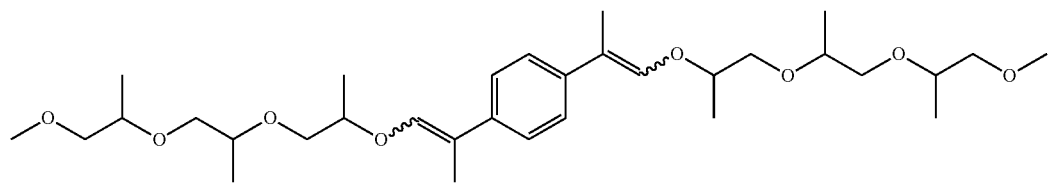
7
,
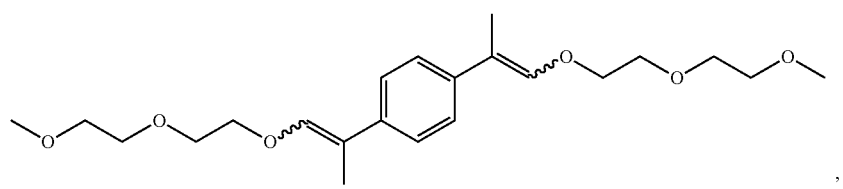
8
,
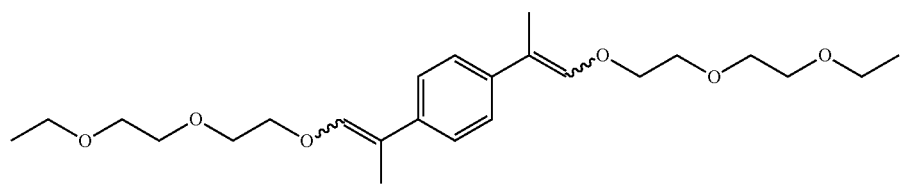
9
,
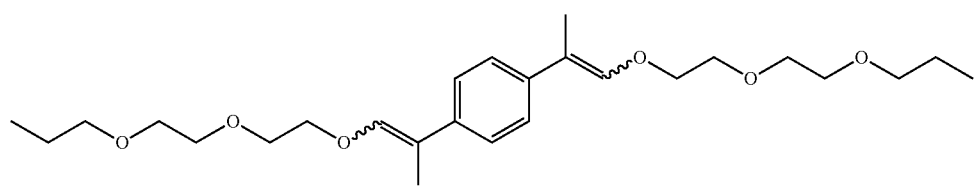
10
,
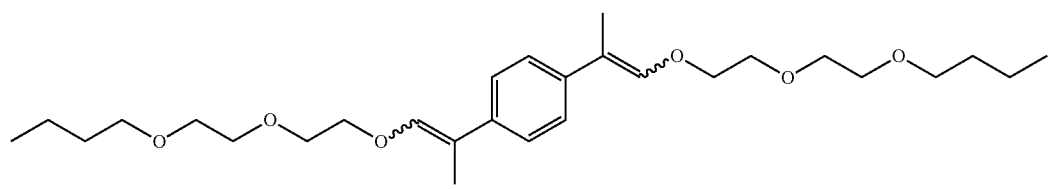
11
,
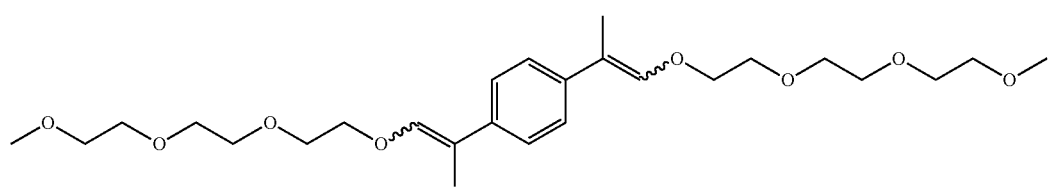
12
,

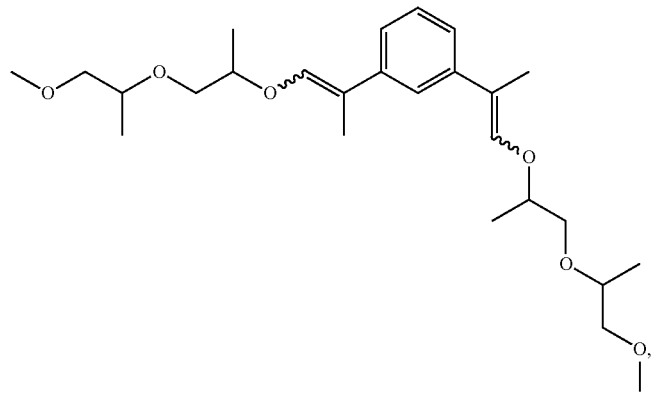
13
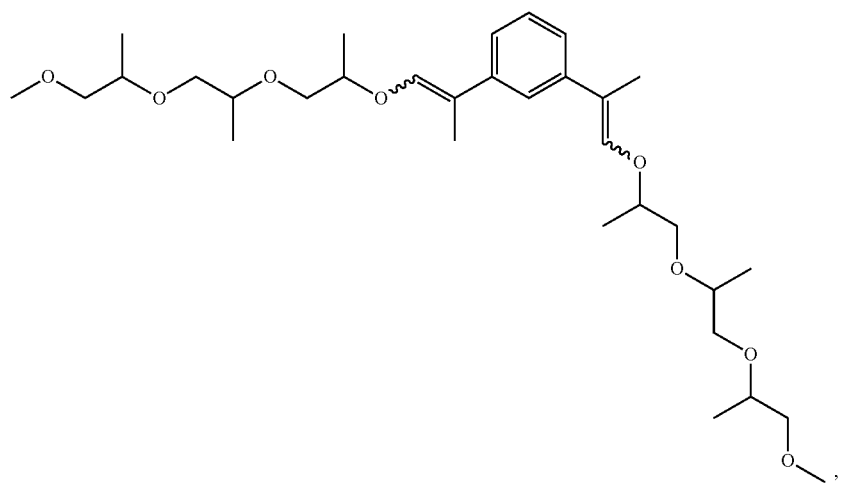
14
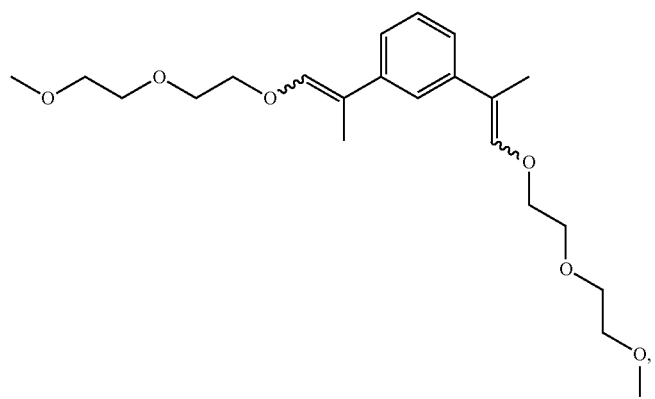
15

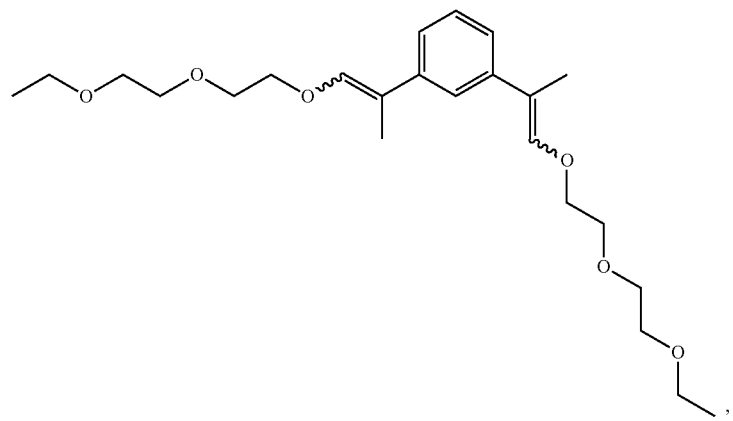
16
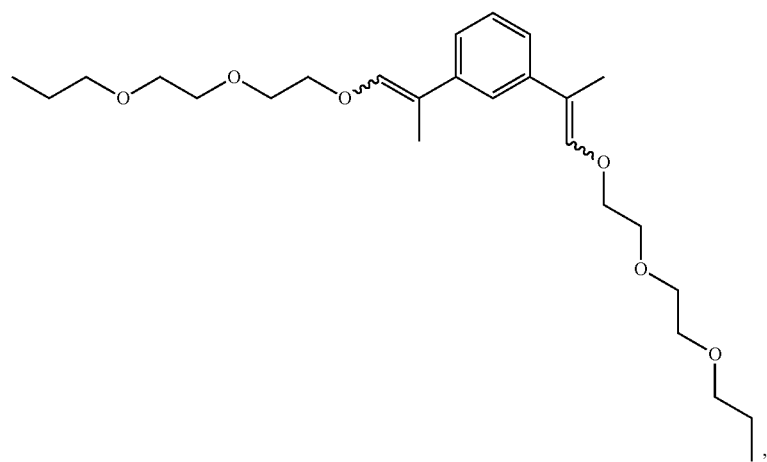
17
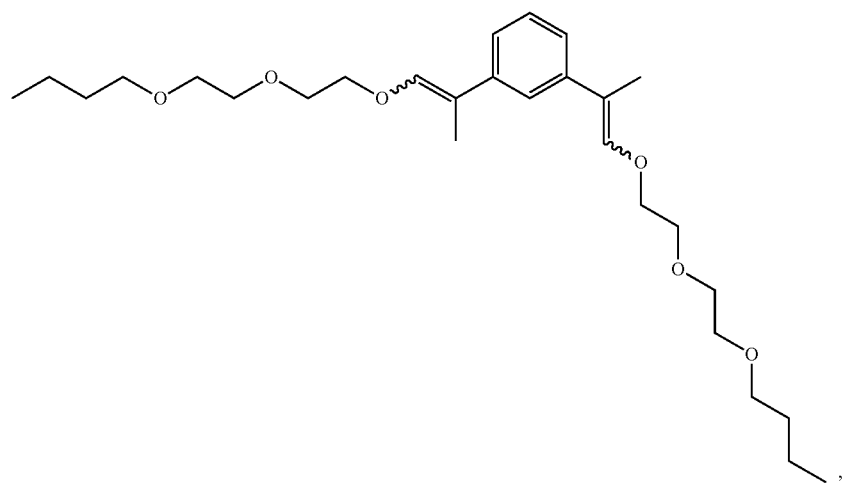
18

-continued
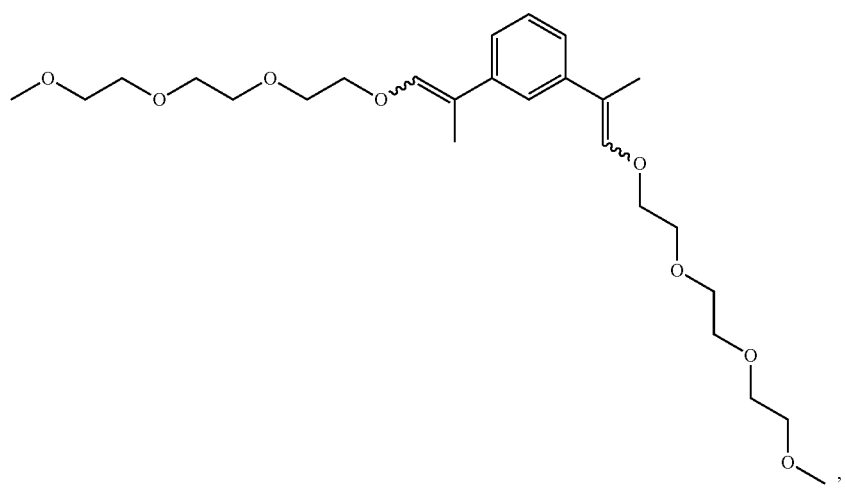
19
and isomers thereof.
* * * * *